United States Patent
Lu et al.

(10) Patent No.: US 10,918,441 B2
(45) Date of Patent: Feb. 16, 2021

(54) DEVICES, SYSTEMS, AND METHODS FOR ABLATION-ZONE SIMULATION AND VISUALIZATION

(71) Applicant: CANON U.S.A., INC., Melville, NY (US)

(72) Inventors: Zhimin Lu, Chelmsford, MA (US); Katsuki Ishii, Belmont, MA (US); Antonio Bonillas Vaca, Boston, MA (US)

(73) Assignee: Canon U.S.A., Inc., Melville, NY (US)

( * ) Notice: Subject to any disclaimer, the term of this patent is extended or adjusted under 35 U.S.C. 154(b) by 160 days.

(21) Appl. No.: 16/194,173

(22) Filed: Nov. 16, 2018

(65) Prior Publication Data

US 2019/0151026 A1    May 23, 2019

Related U.S. Application Data

(63) Continuation-in-part of application No. 15/897,973, filed on Feb. 15, 2018, now Pat. No. 10,751,128.
(Continued)

(51) Int. Cl.
*A61B 34/10* (2016.01)
*A61B 8/00* (2006.01)
(Continued)

(52) U.S. Cl.
CPC .......... *A61B 34/10* (2016.02); *A61B 8/463* (2013.01); *A61B 18/04* (2013.01); *A61B 18/18* (2013.01);
(Continued)

(58) Field of Classification Search
CPC ... A61B 34/10; A61B 2034/104; G06T 15/08; G06F 3/04845
See application file for complete search history.

(56) References Cited

U.S. PATENT DOCUMENTS 8,391,612 B2    3/2013    Natroshvili et al.
8,554,307 B2    10/2013   Razzaque et al.
(Continued)

FOREIGN PATENT DOCUMENTS

EP      2562717 B1       2/2013
JP      2015-500664 A    1/2015
(Continued)

OTHER PUBLICATIONS

Agrafiotis et al., "Virtual Liver Biopsy: Image Processing and 3D Visualization", Proceedings 2001 International Conference on Image Processing, vol. 2, pp. 331-334. (Year: 2001).*
(Continued)

*Primary Examiner* — Nay A Maung
*Assistant Examiner* — Jose M Torres
(74) *Attorney, Agent, or Firm* — Canon U.S.A., Inc. I.P. Division

(57) ABSTRACT

One or more systems, devices, methods and storage mediums are provided herein for ablation-zone simulation, visualization, planning and/or performance. At least one system, device, method and storage medium may obtain an image volume; obtain a description of a surface that includes a shape of the surface, a size of the surface, and a location of the surface in the image volume; sample the image volume on the surface or along a ray from each surface point to another point within the shape, for example, such that sampled surface-image data is or are produced; and generate a visualization of the sampled surface-image data.

29 Claims, 17 Drawing Sheets

Related U.S. Application Data

(60) Provisional application No. 62/590,229, filed on Nov. 22, 2017.

(51) Int. Cl.

| | | |
|---|---|---|
| *G06T 7/10* | (2017.01) | |
| *G06T 7/00* | (2017.01) | |
| *A61B 90/00* | (2016.01) | |
| *A61B 18/00* | (2006.01) | |
| *A61B 34/00* | (2016.01) | |
| *A61B 18/18* | (2006.01) | |
| *A61B 18/04* | (2006.01) | |
| *A61B 18/02* | (2006.01) | |

(52) U.S. Cl.
CPC ............ *A61B 90/37* (2016.02); *G06T 7/0012* (2013.01); *G06T 7/10* (2017.01); *A61B 18/02* (2013.01); *A61B 34/25* (2016.02); *A61B 2018/00577* (2013.01); *A61B 2018/00738* (2013.01); *A61B 2034/104* (2016.02); *A61B 2034/105* (2016.02); *A61B 2034/107* (2016.02); *A61B 2090/378* (2016.02)

(56) References Cited

U.S. PATENT DOCUMENTS

| | | | |
|---|---|---|---|
| 8,670,816 B2 | 3/2014 | Green et al. | |
| 8,805,041 B2 | 8/2014 | Miyamoto | |
| 9,071,745 B2 | 6/2015 | Bocharov et al. | |
| 9,412,176 B2 | 8/2016 | Song et al. | |
| 9,622,813 B2 | 4/2017 | Krugman et al. | |
| 10,102,654 B1 | 10/2018 | Philips et al. | |
| 2005/0033160 A1 | 2/2005 | Yamagata et al. | |
| 2010/0201687 A1* | 8/2010 | Breeuwer ............... | G06T 15/08 345/424 |
| 2010/0312096 A1 | 12/2010 | Guttman et al. | |
| 2011/0026795 A1* | 2/2011 | Leber ..................... | A61B 6/037 382/131 |
| 2011/0251607 A1 | 10/2011 | Kruecker et al. | |
| 2012/0057776 A1 | 3/2012 | Tao et al. | |
| 2012/0189998 A1 | 7/2012 | Kruecker et al. | |
| 2013/0064440 A1 | 3/2013 | Wiemker et al. | |
| 2014/0228835 A1 | 8/2014 | Mielekamp et al. | |
| 2016/0038247 A1 | 2/2016 | Bharadwaj et al. | |
| 2017/0209218 A1 | 7/2017 | Sahay et al. | |
| 2018/0042679 A1 | 2/2018 | Dalal et al. | |
| 2018/0225862 A1 | 8/2018 | Petkov | |
| 2019/0151023 A1 | 5/2019 | Lu et al. | |
| 2019/0328458 A1 | 10/2019 | Shmayahu et al. | |
| 2019/0340837 A1 | 11/2019 | Shmayahu et al. | |

FOREIGN PATENT DOCUMENTS

| | | |
|---|---|---|
| JP | 2016-527994 A | 9/2016 |
| JP | 2017-532078 A | 11/2017 |
| WO | 2009/119908 A1 | 10/2009 |
| WO | 2010/064154 A1 | 6/2010 |
| WO | 2011/128792 A2 | 10/2011 |
| WO | 2012/066449 A1 | 5/2012 |
| WO | 2013/038324 A1 | 3/2013 |
| WO | 2015/148378 A1 | 10/2015 |
| WO | 2016/151111 A1 | 9/2016 |

OTHER PUBLICATIONS

Eva Monclus, et al., "The Virtual Magic Lantern: An Interaction Metaphor for Enhanced Medical Data Inspection", Proceedings of the 16th ACM Symposium on Virtual Reality Software and Technology, Kyoto, Japan, XP058210121, Nov. 18-20, 2009, pp. 119-122.

\* cited by examiner

DEVICES, SYSTEMS, AND METHODS FOR ABLATION-ZONE SIMULATION AND VISUALIZATION

CROSS-REFERENCE TO RELATED APPLICATIONS

This application is a continuation-in-part, and claims the benefit, of U.S. patent application Ser. No. 15/897,973, filed on Feb. 15, 2018, which both claim the benefit of U.S. Provisional Pat. Application No. 62/590,229, which was filed on Nov. 22, 2017, the entire disclosures of which applications are incorporated by reference herein in their entireties.

BACKGROUND

Technical Field

This application generally relates to the simulation, visualization, and planning of medical ablations.

Background

There are various forms of ablation, and successful ablation is made more likely by good planning. Ablation is sometimes ordered after a diagnosis by oncologists who decide that ablation is the best treatment of a lesion or a tumor. An interventional radiologist (IR) may gather and analyze images to accurately characterize tumors and their sizes. Also, an IR may conduct some initial imaging before developing an ablation strategy. The ablation strategy may include selecting an imaging modality, the number of probes, the trajectories of the probe insertions, the probe-insertion points, and the modality of ablation (e.g., microwave, cryo, laser, radiofrequency, high-focused ultrasound).

SUMMARY

Some embodiments of a device comprise one or more processors and one or more computer-readable media that are coupled to the one or more processors. The one or more computer-readable media include instructions for obtaining an image volume; obtaining a description of a surface that includes a shape of the surface, a size of the surface, and a location of the surface in the image volume; sampling the image volume on the surface or along a ray projected from the surface to another point within the shape; applying a function to the sampled values, such that sampled surface-image data are produced; and generating a visualization of the sampled surface-image data. In one or more embodiments, the one or more processors operate to: obtain the image volume; obtain the description of the surface that includes a shape of the surface, the size of the surface, and the location of the surface in the image volume; sample the image volume on the surface or along a ray projected from the surface to another point within the shape; apply a function to the sampled values such that the sampled surface-image data are produced; and generate the visualization of the sampled surface-image data.

Some embodiments of a method comprise obtaining an image volume, wherein the image volume is composed of an image stack; sampling the image volume on a first surface or along a ray from the surface to another point within the shape, and applying a function to the sampled values, for example, such that first sampled surface-image data is or are produced; and generating a visualization of the first sampled surface-image data.

Some embodiments of one or more computer-readable storage media store instructions that, when executed by one or more computing devices, cause the one or more computing devices to perform operations that comprise obtaining an image volume, wherein the image volume is composed of an image stack; obtaining information that describes a first surface, wherein the first surface models a corresponding ablation zone; sampling the image volume on the first surface or along a ray from the surface to another point within the shape, and applying a function to the sampled values, for example, such that first sampled surface-image data is or are produced; and generating an image of the first sampled surface-image data.

According to other aspects of the present disclosure, one or more additional devices, one or more systems, one or more methods and one or more storage mediums using various ablation technique(s) are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein.

DESCRIPTION

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein.

Figure 1:
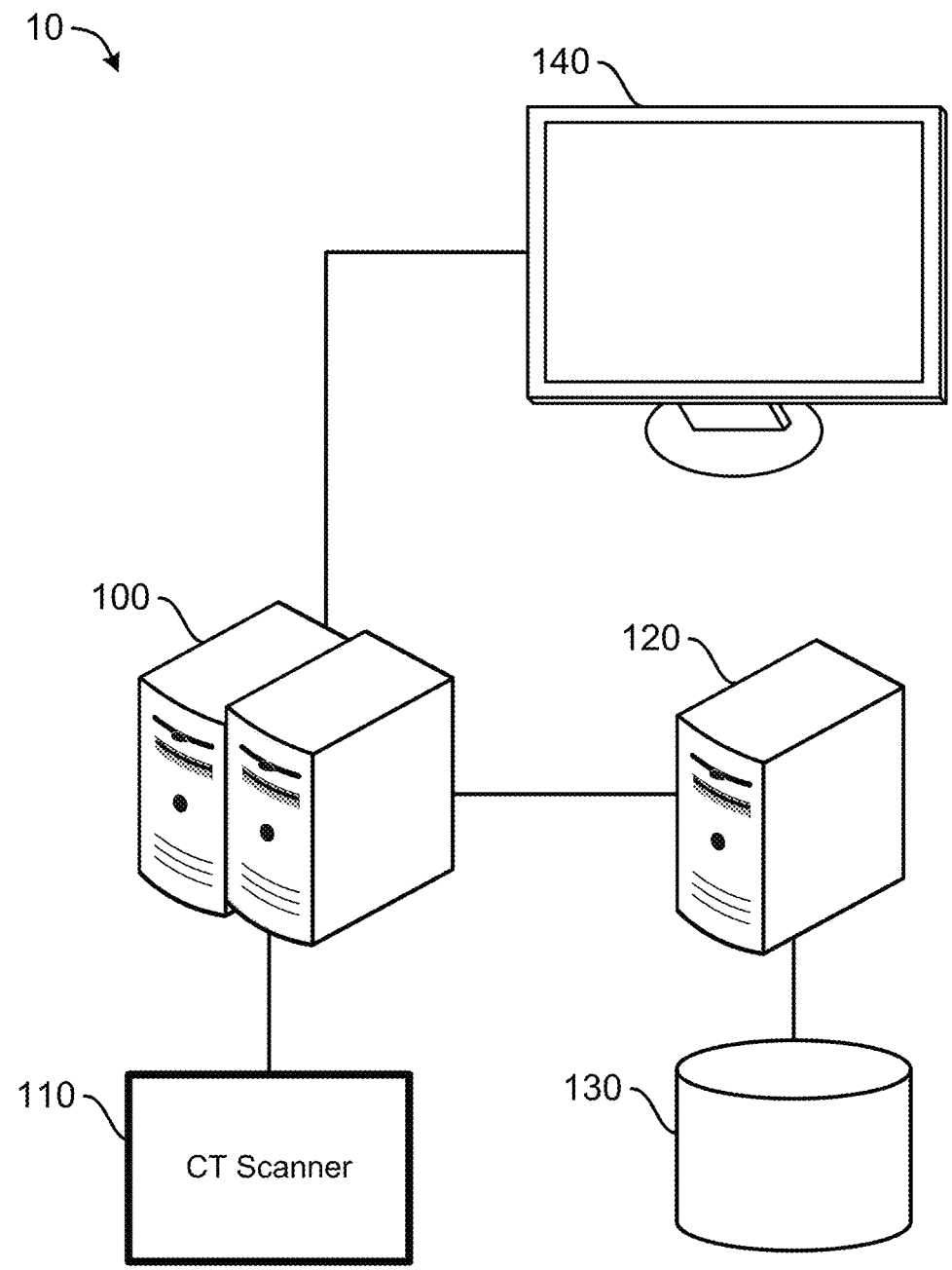
FIG. 1 illustrates an example embodiment of a system for simulating and visualizing an ablation zone.

FIG. 1 illustrates an example embodiment of a system for simulating and visualizing an ablation zone (also referred to herein as a "visualization system"). The visualization system 10 includes one or more simulation devices 100, each of which is a specially-configured computing device (e.g., a specially-configured desktop computer, a specially-configured laptop computer, a specially-configured server); an image-capturing device 110 (which is a CT scanner in this example); an image server 120, which communicates with an image repository 130; and a display device 140. Also, in some embodiments, the image-capturing device 110 is an image-capturing device that is not a CT scanner (e.g., a magnetic-resonance-imaging (MRI) device or an optical coherence tomography (OCT) device).

The one or more simulation devices 100 obtain images from the image-capturing device 110 or the image server 120. The one or more simulation devices 100 then generate a visualization of the images and send the visualization to the display device 140, which displays the visualization.

Figure 2:
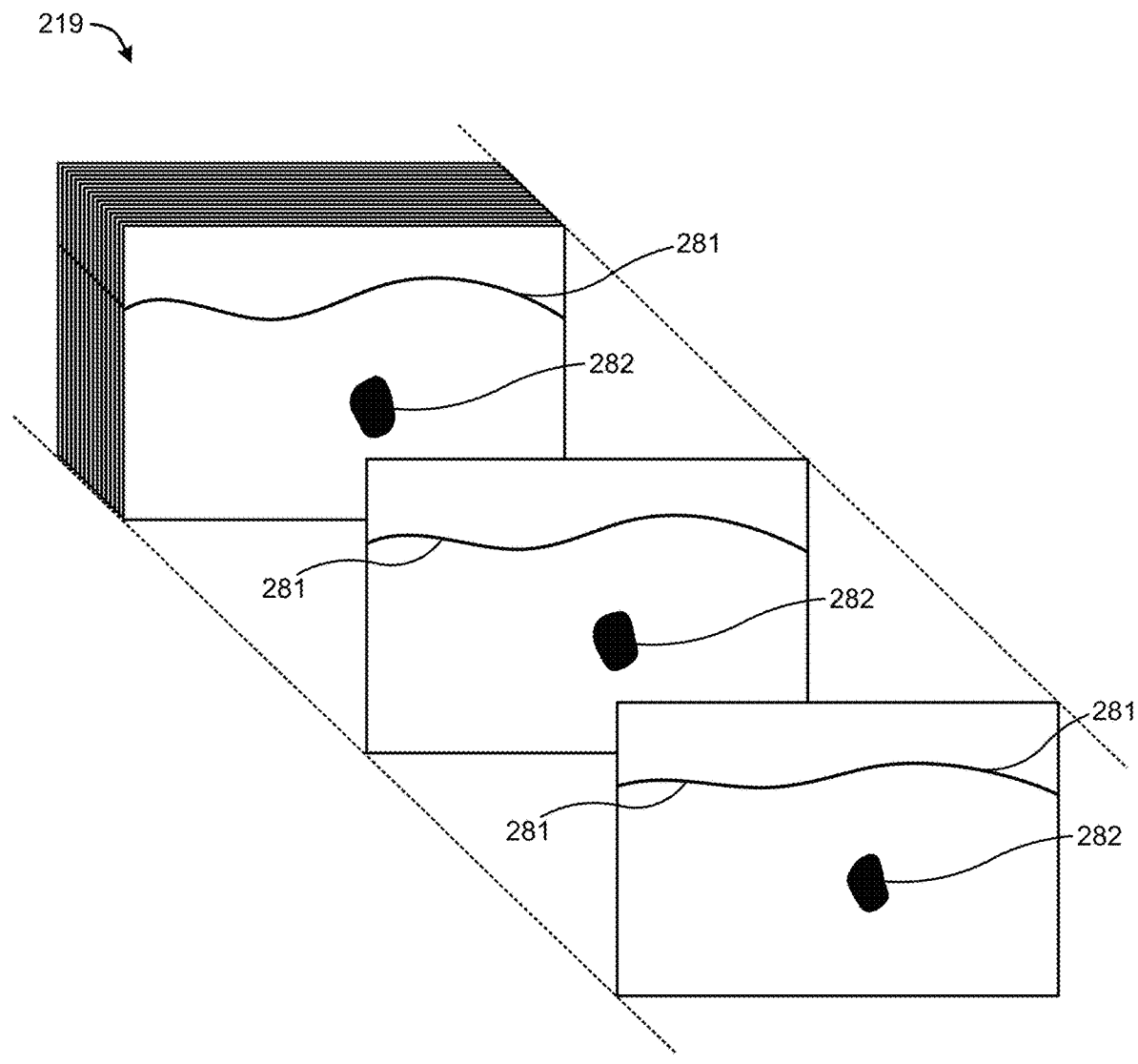
FIG. 2 illustrates an example embodiment of an image volume.

The obtained images may each depict a slice of an object (e.g., a member of a body). For example, the images may each depict a slice of a lung or a liver. The images may be arranged in an image stack that defines a three-dimensional image volume that includes the object. An example of an image volume 219 is shown in FIG. 2. The spaces between three of the images are expanded to increase the visible areas of the images. The images show skin 281 and a tumor 282. When the one or more simulation devices 100 generate a display of the image volume 219, the display may allow a user to change the image that is on top of the volume 219 or the images that are expanded from the volume 219, for example by means of scrolling through the image volume 219.

Figure 13:
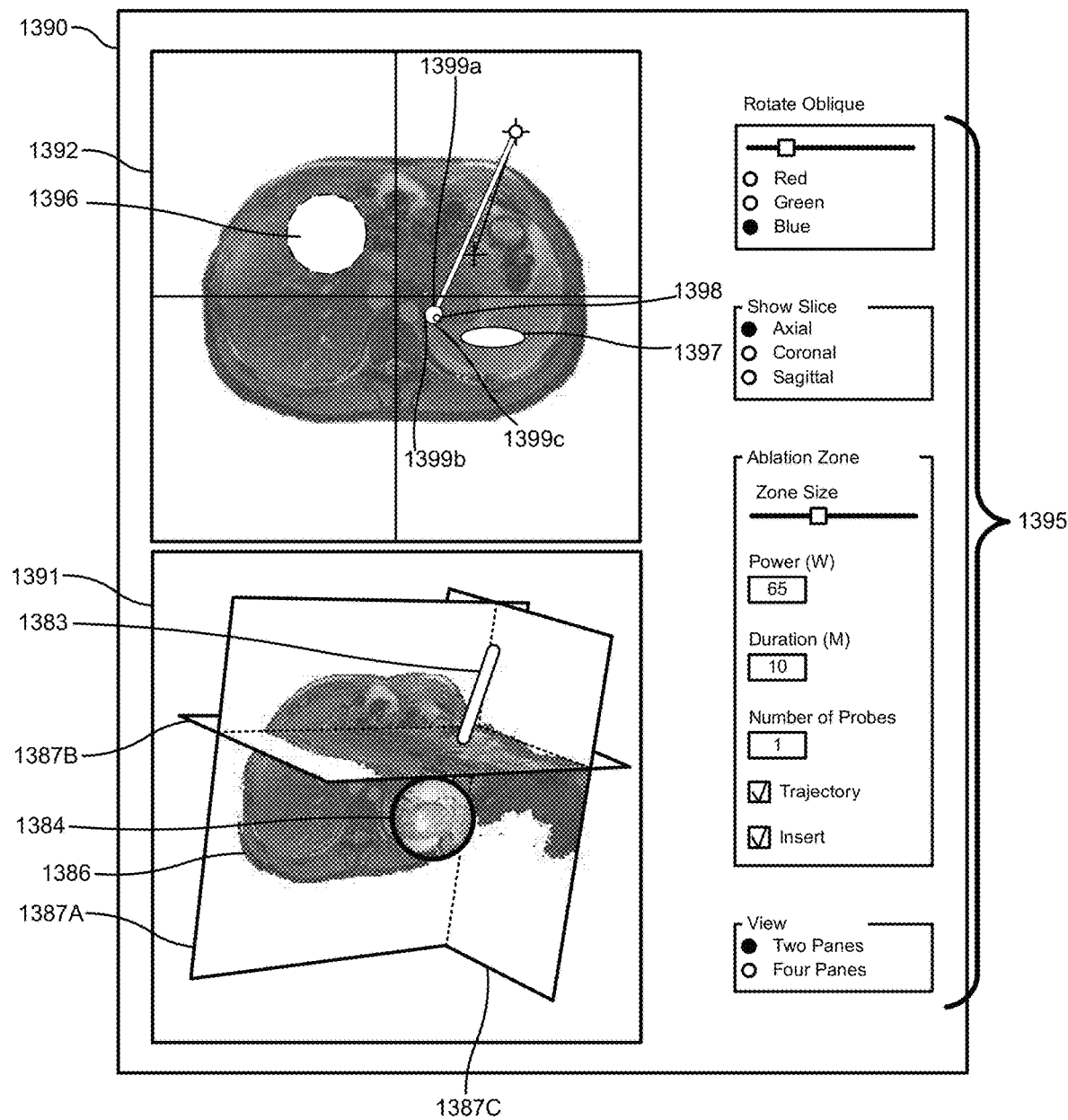
FIG. 13 illustrates an example embodiment of a user interface that includes a visualization of an ablation zone.

The obtained images may be used to generate segmentation maps that label whether each image voxel is part or not of defined anatomical structures (for example tumor (e.g., the tumor 282), organ, bone, skin (e.g., the skin 281), etc.). These segmentation maps may be overlaid on the visualization of the images from the image-capturing device or used for masking the images. For example, as best seen in FIG. 13, at least three (3) segmentation maps 1396, 1397, 1398 are overlaid on the image. Segmentation map 1396 may be used to designate a part of an anatomical structure located outside of the tumor 282 and/or the lantern 1384. The geometric shapes of the segmentation maps may be different depending on the application used (for example, as shown, the segmentation map 1396 may be circular and may use a dashed line (and/or may be shown in a different color compared to another segmentation map); the segmentation map 1397 may be ovular and may be used with a solid line (and/or may be shown in a different color compared to another segmentation map); the segmentation map 1398 may be circular and may use a solid line (and/or may be shown in a different color than one or more other segmentation maps). One or more of the segmentation maps 1396, 1397 may be located outside of the lantern 1384. One or more segmentation maps, such as the segmentation map 1398, may be located inside of the lantern 1384 (e.g., to designate a particular portion of a target, such as the tumor 282). One or more other segmentation maps may be used alternatively or additionally to designate one or more other anatomical structures (e.g., the skin 281, bone, an organ, etc.).

Because an ablation procedure affects a three-dimensional (3D) space, the one or more simulation devices 100 produce a visualization that shows the three-dimensional effects of the ablation procedure. A health-care professional may use the visualization to plan an ablation procedure. For example, a health-care professional may use the visualization to plan the insertion point of a probe, the insertion angle of a probe, the duration of the ablation procedure, and the power of the ablation procedure. The visualization may show the affected three-dimensional space as a sphere, an ellipsoid, or another shape. Also, the affected three-dimensional space may increase in size as the power or duration of the ablation procedure increases and may decrease in size as the power or duration of the ablation procedure decreases. And the type of tissue being ablated, which may also affect the size of the ablation zone, can be simulated.

Figure 3A:
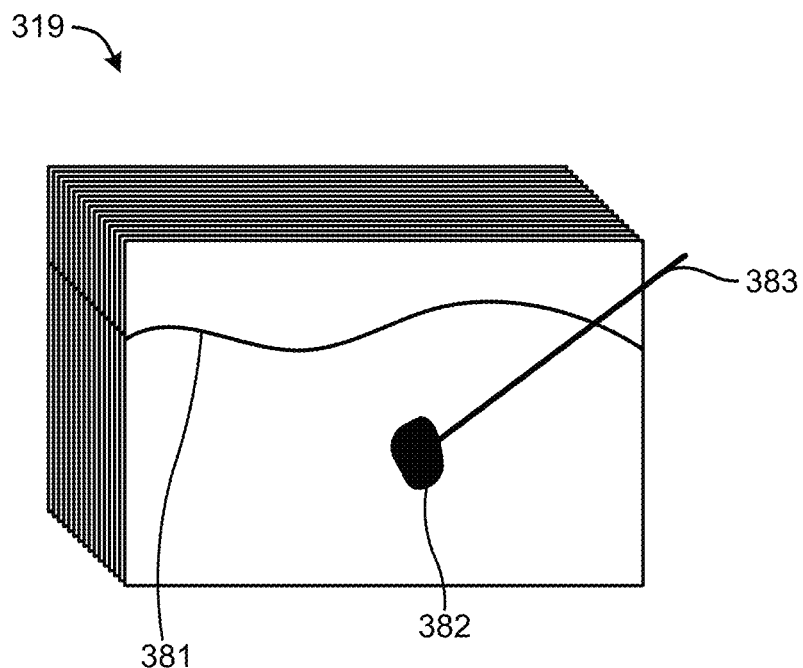
FIG. 3A illustrates an example embodiment of a visualization of an image volume.

FIG. 3A illustrates an example embodiment of a visualization of an image volume 319. This visualization includes a simulation of a probe 383 (e.g., a needle). Accordingly, the visualization shows the approximate position of the probe 383 relative to the skin 381 and the tumor 382.

Figure 3B:
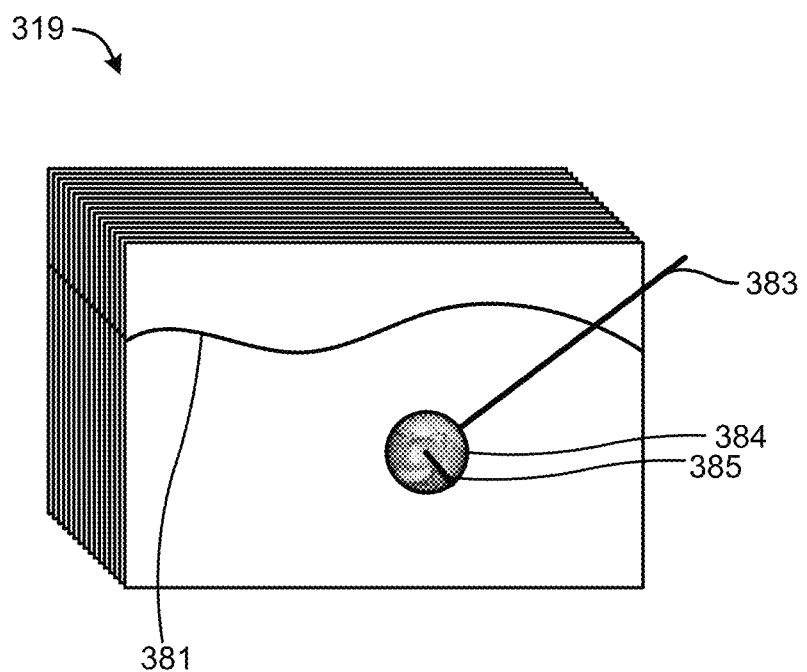
FIG. 3B illustrates an example embodiment of a visualization of an image volume and an ablation zone.

FIG. 3B illustrates an example embodiment a visualization of an image volume 319. This visualization includes a simulation of a probe 383 and a lantern 384, which is a visualization of the surface of an ablation zone. The ablation zone is a volume that may be affected by an ablation procedure. One or more simulation devices 100 calculate the size of the lantern 384 based on one or more of the following: the duration of a simulated ablation procedure, the power of the simulated ablation procedure, a simulated tip of the probe 383, and the material (e.g., tissue) being ablated. In this embodiment, the lantern 384 encompasses the entire tumor 382 from FIG. 3A. Also, in some embodiments, the lantern 384 is deformable, which may allow complex thermal effects to be simulated. For example, some embodiments of user interfaces allow the lantern 384 to be deformed by allowing a user to use a cursor to press on one or a few points on the lantern 384. As discussed further below, an image volume may be taken or sampled from or along a ray 385 (as best shown in FIG. 3B) that passes through or extends from a surface of the lantern 384, or otherwise interacts with the lantern 384.

Some embodiments of the one or more simulation devices 100 perform at least the following operations: (A) obtain an image volume (e.g., a CT volume or an MRI volume); (B) generate a visualization of the image volume; (C) generate a geometrical functional that models the ablation zone (e.g., a sphere, an ellipsoid, a cone); (D) sample (e.g., resample) the image volume on the surface of the generated geometrical functional; (E) reconstruct the image on the surface of the generated geometrical functional, which may include mapping the sampled image volume onto the surface of the ablation zone, for example, such that a lantern is generated (the simulated ablation zone that has an image on its surface); (G) display the lantern, which may be overlaid on the original image volume; and (H) provide an interaction mechanism (e.g., a graphical user interface (GUI)) between the lantern and the image volume such that users can manipulate the size, shape, and location of the lantern. Also, in some embodiments, the lantern can be manipulated arbitrarily (e.g., zoomed in, zoomed out, moved, rotated) by means of a GUI.

Accordingly, displaying the contents of the image volume using a lantern may show the contents of the image volume in a more-accurate form, which gives health-care professionals a view that they can use to plan an ablation procedure. Also, the lantern shows the interaction between the ablation zone and the anatomy adjacent to the ablation zone. Health-care professionals may not need to measure the distance from the ablation zone to other features because health-care professionals can see the features that intersect with the ablation zone by looking at the surface of the lantern. Also, these embodiments allow complex interactions to be visualized at the same time. For example, some embodiments simultaneously show multiple lanterns, which may allow a health-care professional to fine-tune an ablation procedure. Also, these embodiments may allow a health-care professional to move the lantern to a desired procedure location and then determine the center of the ablation zone for the insertion of the probe or to optimize the insertion point of the probe.

Figure 17:
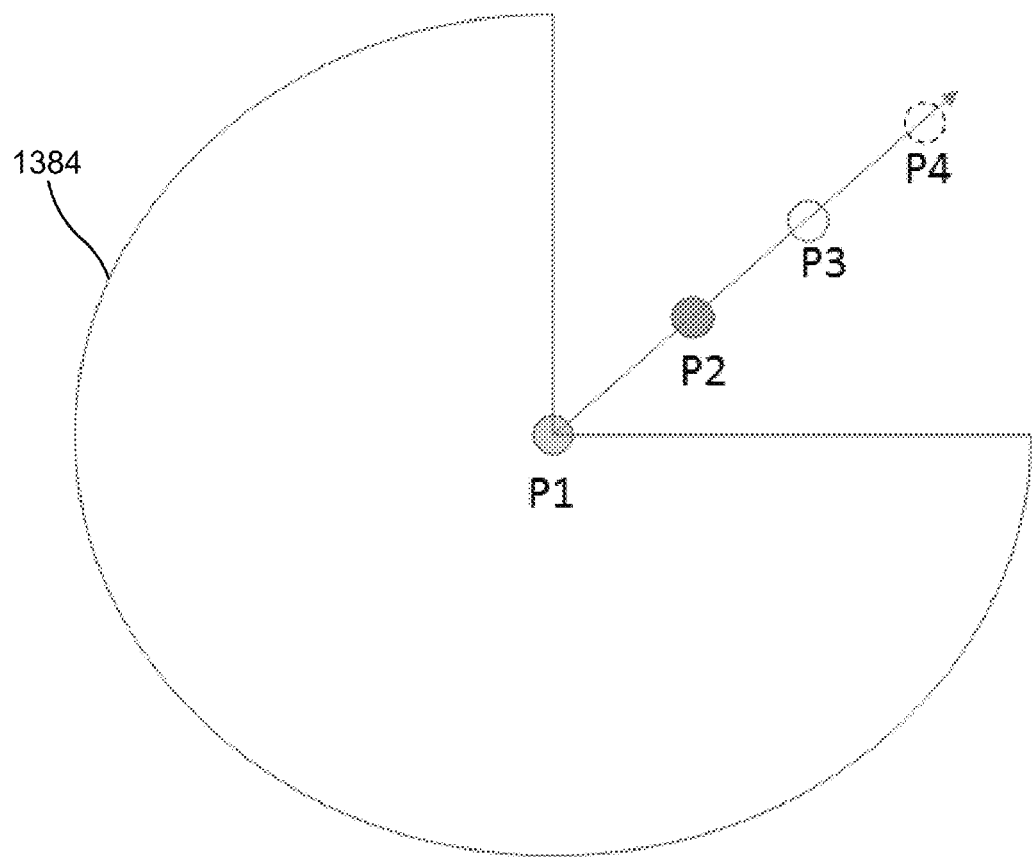
FIG. 17 illustrates an example embodiment of a hallowed out and zoomed in view of at least one lantern in accordance with one or more aspects of the present disclosure.

In alternative embodiments the lantern can display, in place of the value of the immediate data point to the lantern surface, a value calculated from a function applied to a sampling of the data points along a ray from the lantern surface to another point in the lantern region, for example its center or another surface point (see e.g., the ray 1385 as shown in FIG. 3B; see e.g., points P1, P2, P3, P4 along a ray (such as, but not limited to, the ray 1385) of FIG. 17). This function can be for example a maximum, minimum or average value of the sampled data points, for example, such that the health-care professional is provided with a view of what is inside of the ablation zone. As best seen in FIG. 17, at least one embodiment of a lantern (such as the lantern 1384) may be presented in a hollowed out and zoomed in depiction of the lantern view. In at least this example, a ray (e.g., the ray 1385) is shown extending from a center (e.g., where point P1 is located) of the lantern to a surface of the lantern (e.g., the lantern 1384). In one or more embodiments, the ray, such as the ray 1385, may be oriented in other ways, and is not limited to the embodiment configuration shown in FIG. 17. Points P1, P2, P3, P4 along the ray of FIG. 17 illustrate at least one embodiment of a sampling of data points taken along the ray from the lantern surface to another point in the lantern region (e.g., a center of the lantern). As aforementioned, point P1 may be located at the center of the lantern (e.g., the lantern 1384). Points P1, P2, P3 may be filled in with different intensities (e.g., point P1 is lighter than point P2 to depict that the intensity of point P2 is greater than that of P1; the point P3 may be lighter than P1 and P2 to depict that the intensity of P3 is less than the respective intensities of points P1, P2; etc.) in order to depict different values. Point P4 may be located at the surface of the lantern (e.g., the lantern 1384), and may be filled in with a corresponding value (depiction shown with a dashed line) at the surface of the lantern (e.g., the lantern 1384). In one or more embodiments, however, a surface value may not accurately provide context for values located below the surface of the lantern (e.g., the lantern 1384). As such, in one or more embodiments, a function may be applied (e.g., along a ray, such as the ray 1385) to accurately provide values and context for points located below the surface of the lantern (e.g., the lantern 1384). As discussed herein, one or more examples of such a function may include, but is not limited to, a maximum of sampled points (e.g., a predetermined maximum distance of sampled points, a predetermined maximum number of sampled points, etc.), in which case point P4 may be filled in with the shading from point P2. A minimum value function may have point P4 taking in the value from point P3. An average function value may average the values of points P1 to P3, and represent that as the appropriate value or shaded intensity within point P4. The chosen function (or other function that may be used) may be application dependent, or may be set by a user. Tumor objects represented in CT images are not uniform; tumor objects are composed of gradients of intensities, and the composition of such tumor objects may change depending on a geography of interest. As such, segmentation maps (e.g., the segmentation maps 1396, 1397, 1398, etc.) may change shape or may have a non-uniform shape over time depending on the geography of interest. The segmentation maps or other segmentation maps (e.g., the maps 1396, 1397, etc.) may be different structures of an organ (e.g., liver structure 1, liver structure 2, etc.) that is being targeted in a medical procedure or application.

Other embodiments may display in the lantern a value relative to a sampling of segmentation maps on the surface of the lantern or along a ray from the surface to another point in the lantern region, for example, such that it is indicated whether a segmented anatomical region is contained in the sampled points, or the distance from the surface of the anatomical region to the surface of the lantern. For example, as shown in the top part of FIG. 13, points 1399a, 1399b, 1399c, which are a sampling of values on the surface of the lantern 1384, may be used to obtain the value. As aforementioned, points P1 through P4 may be taken along a ray (e.g., the ray 1385) to obtain the value. Regardless of the location of the sampling of data points, the value that is obtained may be obtained in any meaningful way, such as, but not limited to, using different intensities, geometric shapes, dashed or solid lines, different colors, displaying the value as a number in the image, etc.

Figure 4A:
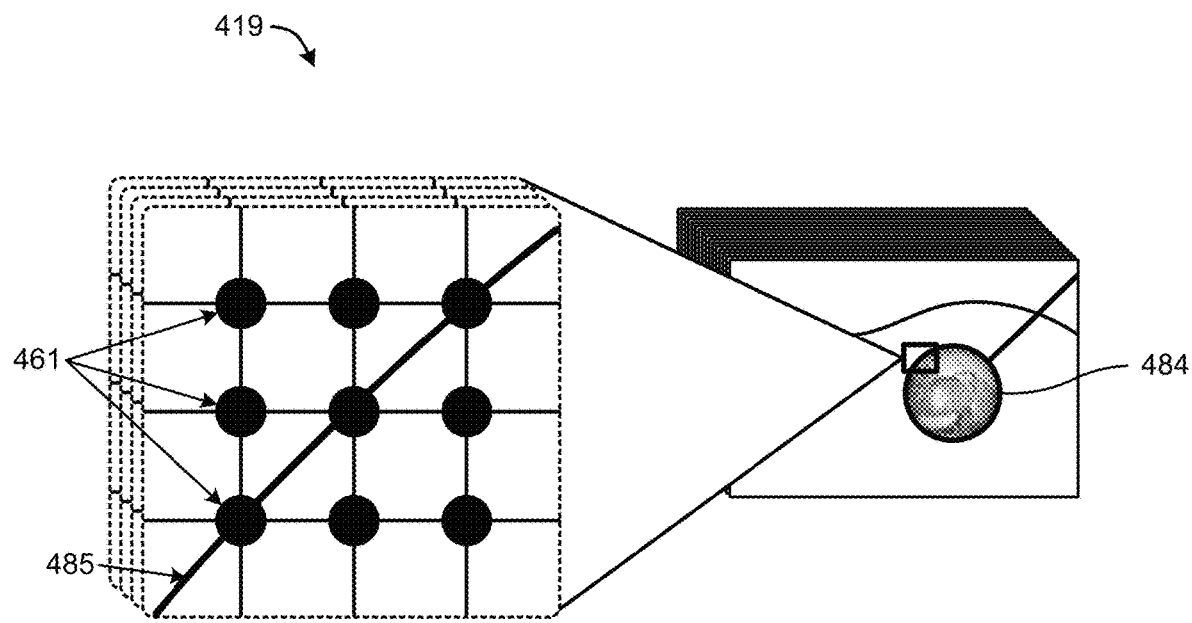
FIG. 4A illustrates an example embodiment of a set of data points and a surface of an ablation zone.

FIG. 4A illustrates an example embodiment of a set of data points in an image volume and a surface of an ablation zone. The data points 461 collectively define an image volume 419 (note that, although not all of the data points are labeled, the solid-black circles all represent respective data points). For example, each data point 461 may be a respective pixel, and each image may form a respective plane of pixels in the image volume. Also, the surface 485 of the ablation zone 484 passes through or close to three of the data points 461. Thus, the one or more simulation devices 100 can use these three data points 461 when sampling image data on the surface 485 of the ablation zone.

Figure 4B:
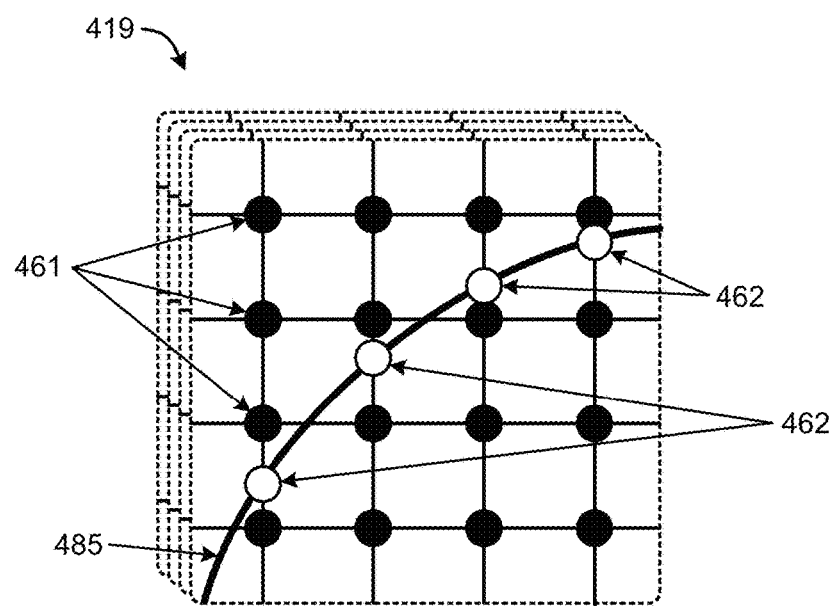
FIG. 4B illustrates an example embodiment of a set of data points and a surface of an ablation zone.

FIG. 4B illustrates an example embodiment of a set of data points in an image volume and a surface of an ablation zone. The data points 461 collectively define an image volume 419. However, in this example, the ablation zone's surface 485 does not pass through or close to any of the data points 461. Thus, when sampling the image volume 419 on the surface 485, the one or more simulation devices 100 use interpolated data points 462. Depending of the path of the surface 485, the one or more simulations devices 100 can use both data points 461 and interpolated data points 462 when sampling the image volume 419 on the surface 485.

Figure 5A:
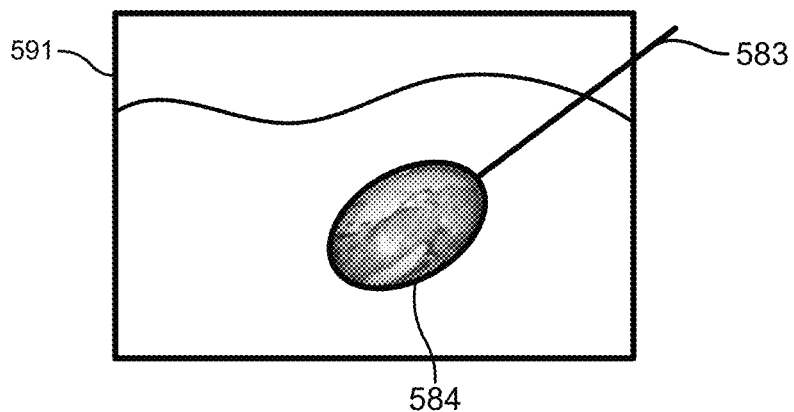
FIG. 5A illustrates an example embodiment of a display that shows an ablation zone.

FIG. 5A illustrates an example embodiment of a display that shows an ablation zone. In the display 591 in FIG. 5A, the ablation zone 584 is not spherical. A non-spherical ablation zone may be produced by the shape of the tip of the probe 583.

Figure 5B:
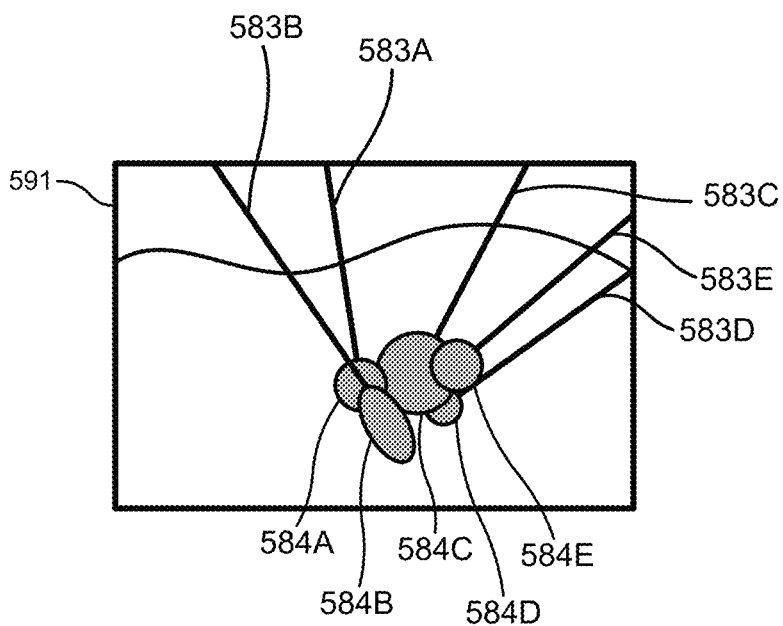
FIG. 5B illustrates an example embodiment of a display that shows multiple ablation zones and multiple probes.

FIG. 5B illustrates an example embodiment of a display that shows multiple ablation zones. This embodiment of a display 591 shows multiple probes 583A-E, each of which produces a respective ablation zone 584A-E. Multiple ablation zones 584A-E can be combined to produce more-complex shapes. For example, the ablation zones 584A-E may be combined by a union operation to form a shape that is more complex than any one of the ablation zones 584A-E.

Figure 6:
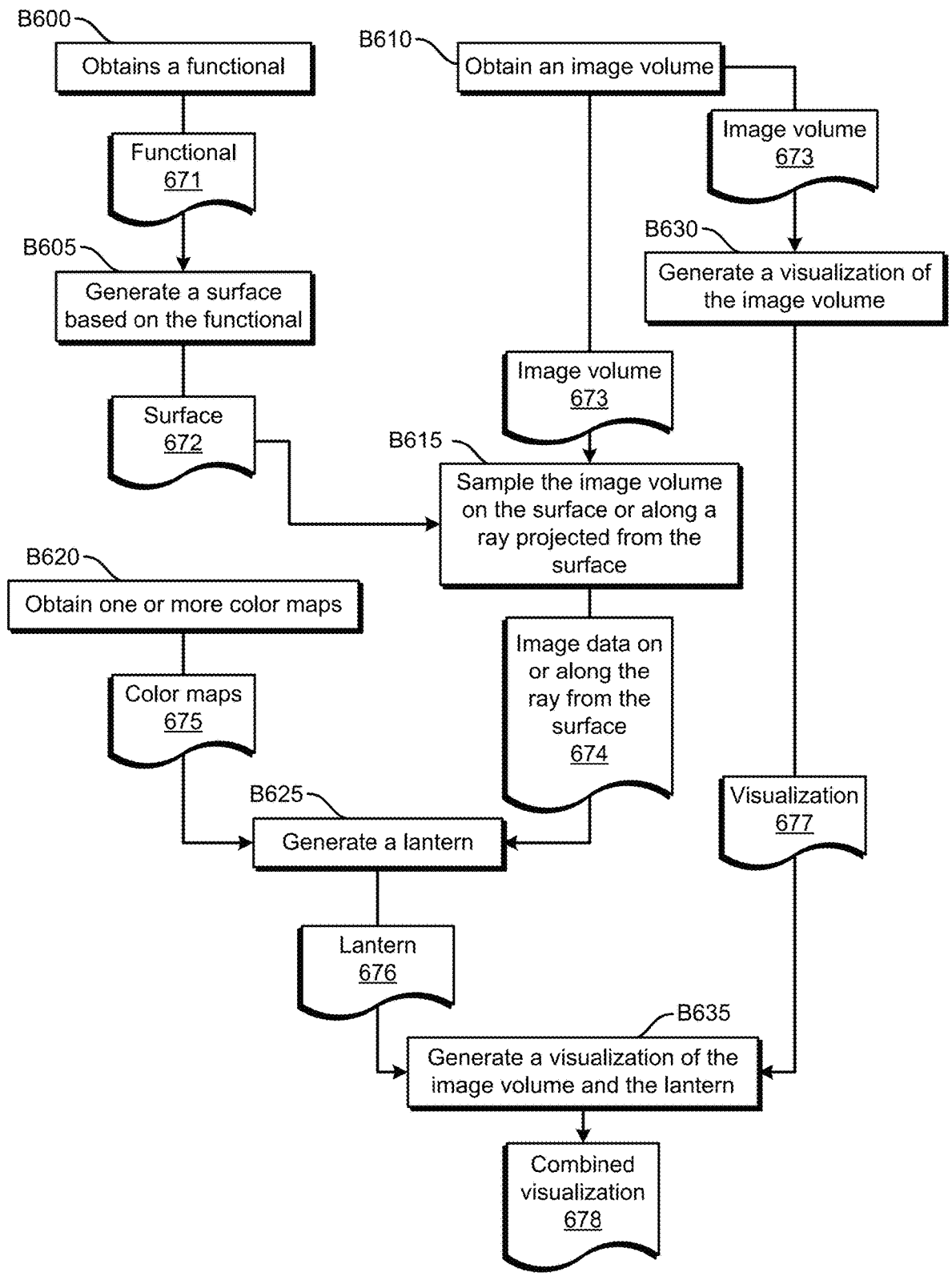
FIG. 6 illustrates an example embodiment of an operational flow for visualizing an ablation zone.

FIG. 6 illustrates an example embodiment of an operational flow for visualizing an ablation zone. Although this operational flow and the other operational flows that are described herein are each presented in a certain order, some embodiments may perform at least some of the operations in different orders than the presented orders. Examples of different orderings include concurrent, parallel, overlapping, reordered, simultaneous, incremental, and interleaved orderings. Thus, other embodiments of the operational flows that are described herein may omit blocks, add blocks, change the order of the blocks, combine blocks, or divide blocks into more blocks.

Furthermore, although this operational flow and the other operational flows that are described herein are performed by a simulation device, some embodiments of these operational flows are performed by two or more simulation devices or by one or more other specially-configured computing devices.

The operational flow in FIG. 6 includes a first flow, a second flow, a third flow, and a fourth flow. The first flow starts in block B600, where the simulation device obtains (e.g., receives, generates) a functional 671, which defines a shape. The functional 671 may describe or model the relationships between the shape of an ablation zone and the following: a time of an ablation procedure, a power of the ablation procedure, a shape of the ablation zone, and the composition of the material that will be ablated.

Next, in block B605, the simulation device generates a surface 672 based on the functional. The first flow then moves to block B615, where it merges with the second flow to form a combined flow.

The second flow starts in block B610, where the simulation device obtains an image volume 673. The second flow then proceeds to block B615, where it merges with the first flow to form the combined flow.

In block B615, the simulation device samples the image volume 673 on, or along a ray projected from, the surface and outputs the image data on, or along the ray projected from, the surface 674 (e.g., the ray may project through the lantern). In block B615, the simulation device may interpolate image data in areas where the surface, or the ray projected from the surface, is not close to the data points in the image volume 673, for example as illustrated in FIG. 4B. The combined flow then proceeds to block B625, where it merges with the third flow.

The third flow starts in block B620, where the simulation device obtains one or more color maps 675. The third flow then moves to block B625, where it merges with the combined flow. In block B625, the simulation device reconstructs the image data on the surface, for example, such that a lantern 676 (a surface with image data from the image volume 673) is produced, based on the color maps 675 and on the image data on, or along the ray projected from, the surface 674. The combined flow then moves to block B635, where it merges with the fourth flow.

The fourth flow starts in block B610 and moves to block B630, where the simulation device generates a visualization 677 of the image volume 673. The fourth flow then proceeds to block B635, where it merges with the combined flow.

In block B635, the simulation device generates a combined visualization 678 based on the lantern 676 and on the visualization 677 of the image volume 673. Examples of a combined visualization 678 are shown in FIGS. 10A, 10B, 11, 11, 12, 13, 14B, and 15A-D.

Figure 7:
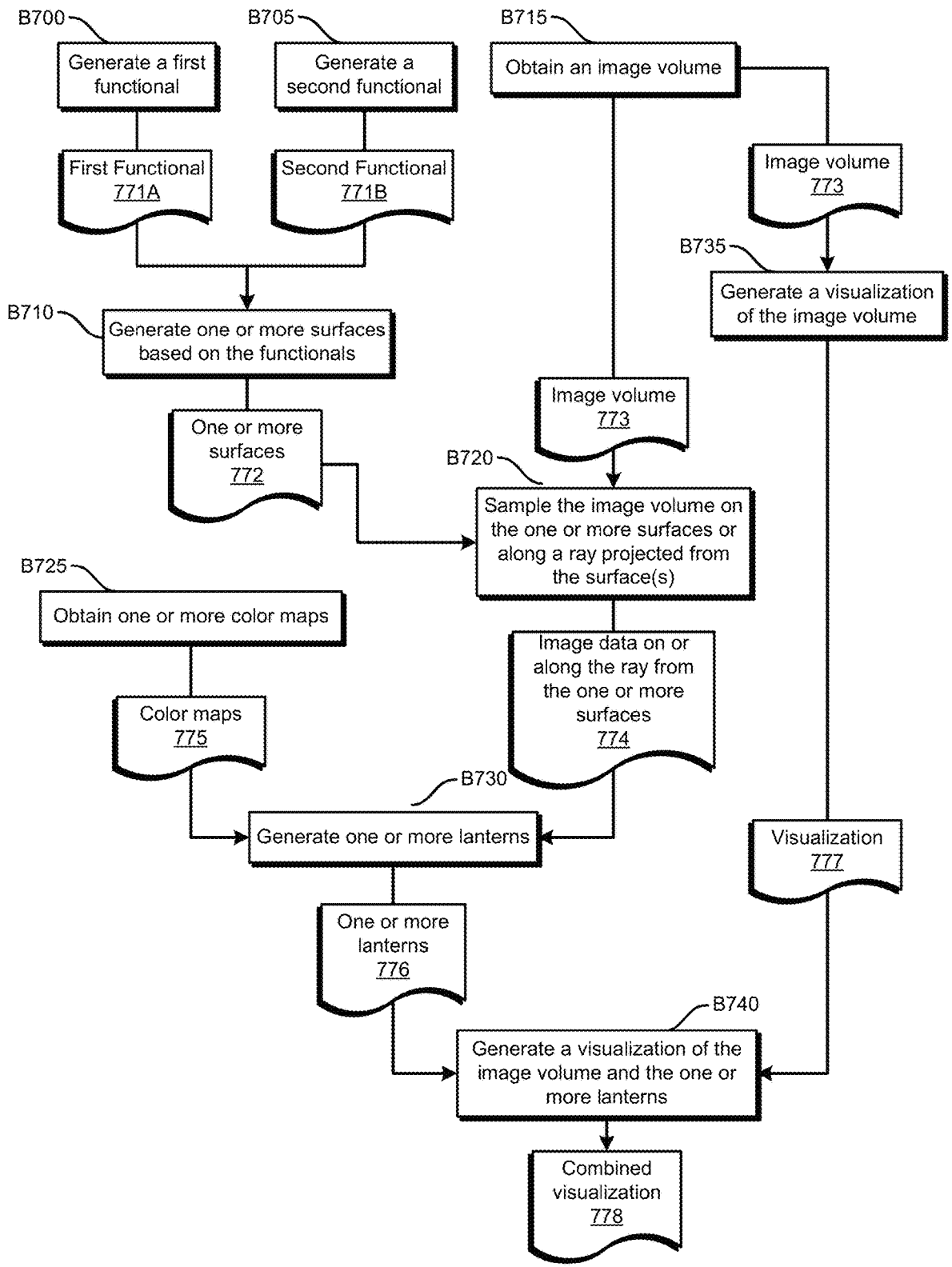
FIG. 7 illustrates an example embodiment of an operational flow for visualizing an ablation zone.

FIG. 7 illustrates an example embodiment of an operational flow for visualizing an ablation zone. The operational flow in FIG. 7 includes a first flow, a second flow, a third flow, a fourth flow, and a fifth flow. The first flow starts in block B700, where the simulation device obtains (e.g., receives, generates) a first functional 771A, which defines a shape, and then proceeds to block B710, where it merges with the second flow to form a combined flow.

The second flow starts in block B705, where the simulation device obtains a second functional 771B, and then the second flow moves to block B710, where it merges with the first flow to form a combined flow.

In block B710, the simulation device generates one or more surfaces 772 (e.g., the surface of an ablation zone) based on the first functional 771A and on the second functional 771B. For example, some embodiments of the simulation device use a union operation to merge the first functional 771A and the second functional 771B into a single surface if the first functional 771A and the second functional 771B overlap and do not merge the first functional 771A and the second functional 771B into a single surface if the first functional 771A and the second functional 771B do not overlap. The combined flow then moves to block B720, where it merges with the third flow.

The third flow starts in block B715, where the simulation device obtains an image volume 773 (e.g., an image volume). The third flow then proceeds to block B720, where it merges with the combined flow.

In block B720, the simulation device samples (e.g., resamples) the image volume 773 on, or along a ray projected from, the one or more surfaces 772 (e.g., the ray may project through the lantern), for example, to produce the image data on, or along the ray projected from, the one or more surfaces 774. In block B720, the simulation device may interpolate image data in areas where the surface, or the ray projected from the surface(s), is not close to the data points in the image volume, for example as illustrated in FIG. 4B and in FIG. 8. The combined flow then proceeds to block B730, where it merges with the fourth flow.

The fourth flow starts in block B725, where the simulation device obtains one or more color maps 775. The fourth flow then moves to block B730, where it merges with the combined flow. In block B730, the simulation device generates one or more lanterns 776 based on the color maps 775 and on the resampled image data 774. The combined flow then moves to block B740, where it merges with the fifth flow.

The fifth flow starts in block B715 and moves to block B735, where the simulation device generates a visualization 777 of the image volume 773. The fifth flow then proceeds to block B740, where it merges with the combined flow.

In block B740, the simulation device generates a combined visualization 778 based on the one or more lanterns 776 and on the visualization 777 of the image data 773. Examples of a combined visualization 778 are shown in FIGS. 10A, 10B, 11, 11, 12, 13, 14B, and 15A-D.

Figure 8:
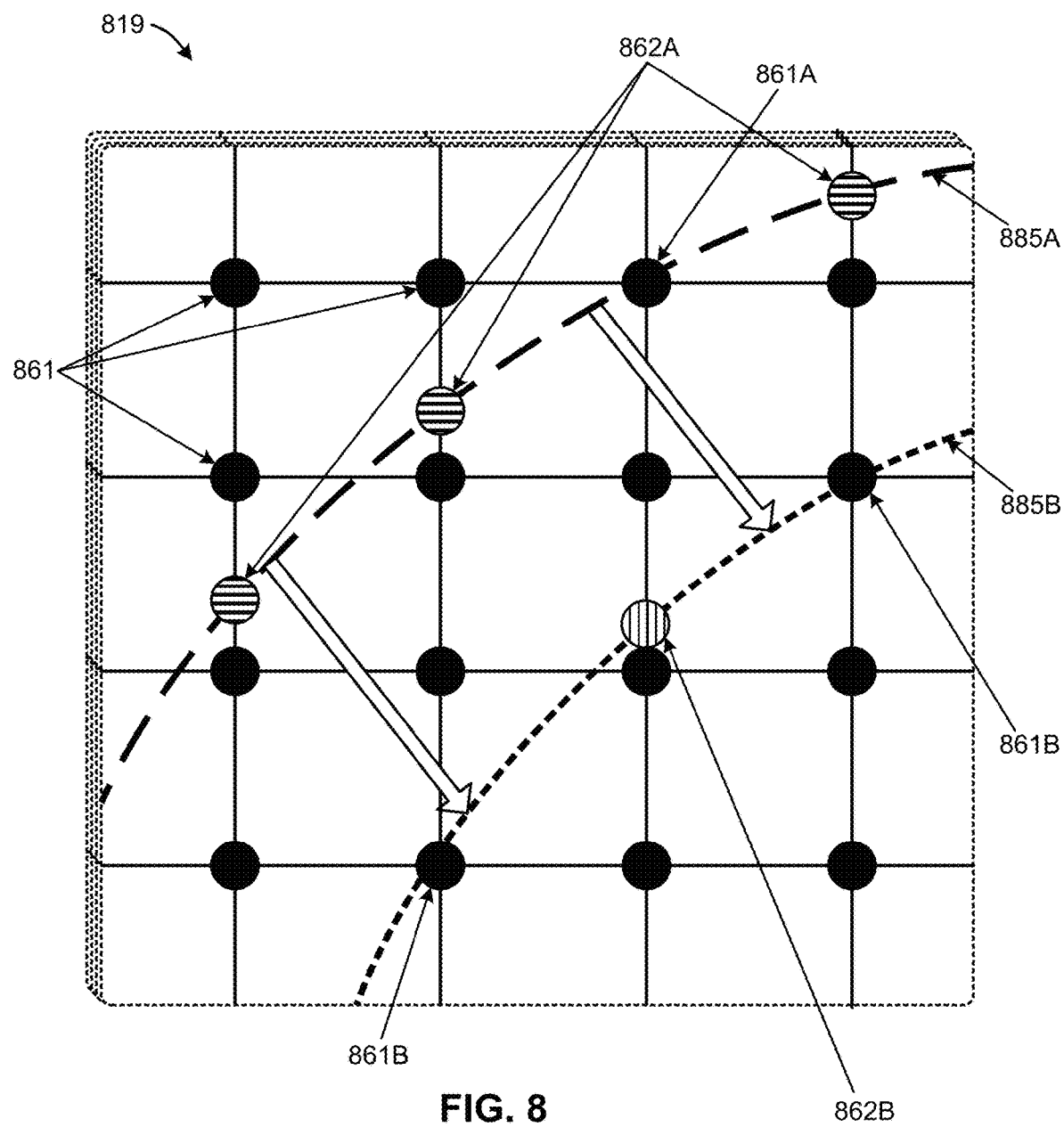
FIG. 8 illustrates an example embodiment of a set of data points in an image volume and a surface of an ablation zone.

FIG. 8 illustrates an example embodiment of a set of data points in an image volume and a surface of an ablation zone. The set includes data points 861 that collectively define an image volume 819. Also, FIG. 8 shows a first surface 885A of an ablation zone and shows a second surface 885B that is generated in response to a modification of the ablation zone. For example, the size or the position of the ablation zone may be changed. The first surface 885A of the ablation zone passes through or very close to one data point 861A in the image volume 819. To acquire image data for the rest of the illustrated surface, three interpolated data points 862A are generated.

The modification of the ablation zone produces the second surface 885B. Because the location of the second surface 885B in the image volume 819 is different from the location of the first surface 885A, new data points are obtained for the second surface 885B. The second surface passes through or close to two data points 861B. To acquire image data for the rest of the surface that is shown in FIG. 8, an interpolated data point 862B is generated based on the neighboring data points 861. Thus, the image data for the first surface 885A illustrates the image volume at the location of the first surface 885A, and the image data for the second surface 885B illustrates the image volume at the location of the second surface 885B. Accordingly, the image on the second surface 885B is different from the image on the first surface 885A.

Figure 9:
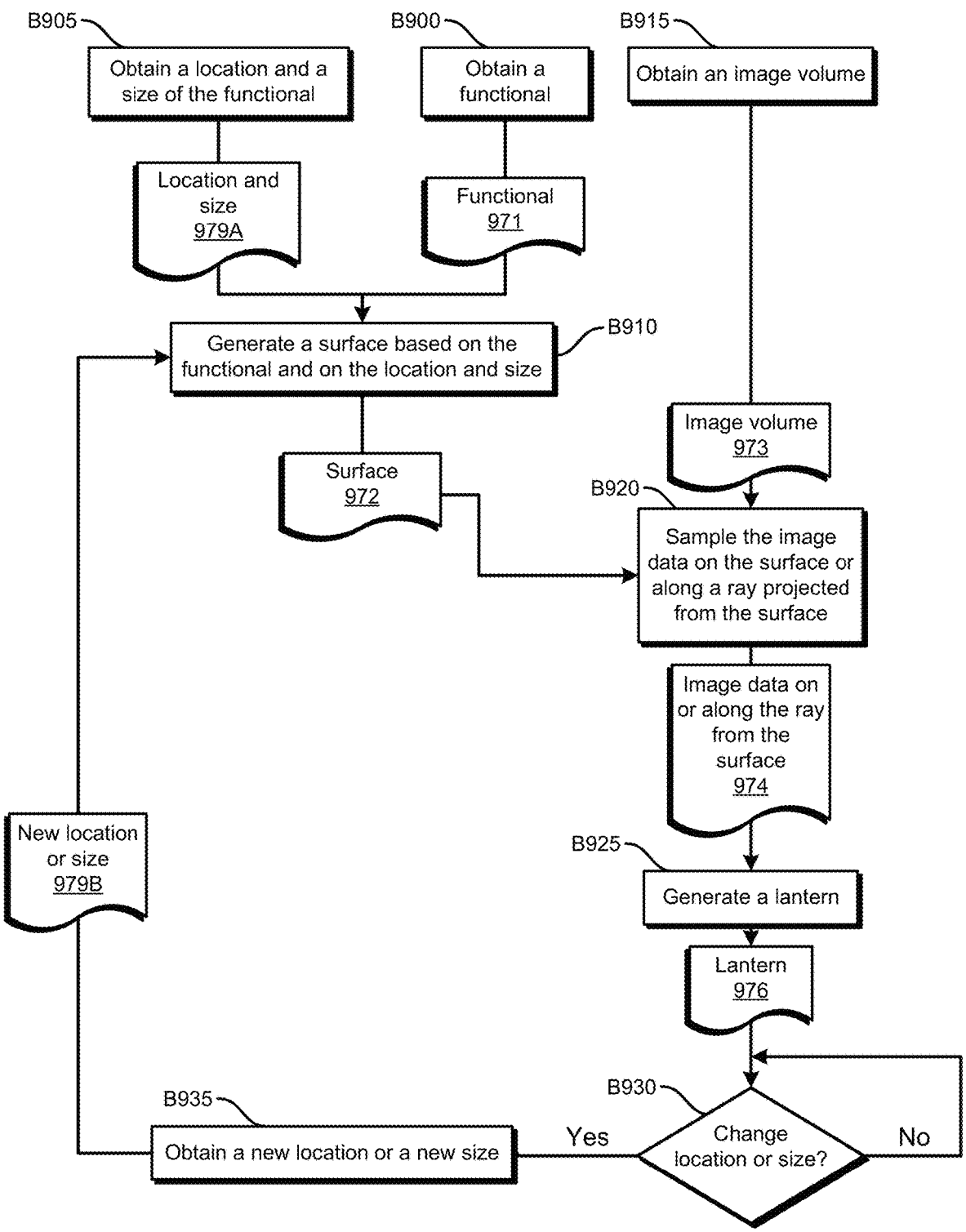
FIG. 9 illustrates an example embodiment of an operational flow for visualizing an ablation zone.

FIG. 9 illustrates an example embodiment of an operational flow for visualizing an ablation zone. The operational flow in FIG. 9 includes a first flow, a second flow, and a third flow. The first flow starts in block B900, where a simulation device obtains a functional 971. The first flow then moves to block B910, where it merges with the second flow.

The second flow starts in block B905, where the simulation device obtains a location and a size 979A of an ablation zone. The second flow then proceeds to block B910, where it merges with the first flow, for example, to produce a combined flow.

In block B910, the simulation device generates a surface 972 based on the functional 971 and on the location and size 979A. The combined flow then moves to block B920, where it merges with third flow.

The third flow starts in block B915, where the simulation device obtains an image volume 973. The third flow then proceeds to block B920, where it merges with the combined flow.

In block B920, the simulation device samples the image volume 973 on, or along a ray projected from, the surface 972, for example, to produce the image data on, or along the ray projected from, the surface 974 (e.g., the ray may project through the lantern). Next, in block B925, the simulation device generates a lantern 976 based on the image data on, or along the ray projected from, the surface 974 (e.g., the ray may project through the lantern).

The combined flow then moves to block B930, where the simulation device determines if the location or size of the lantern should be changed. If not (block B930=No), then the combined flow waits at block B930. If the location or the size should be changed (block B930=Yes), for example in response to a user input, then the flow moves to block B935. For example, the location or the size may be changed in response to a command to move an ablation zone, a command to resize an ablation zone, or a command to change the functional that defines an ablation zone.

In block B935, the simulation device obtains a new location or a new size 979B of the lantern. This may include obtaining a new shape of the surface. And in some embodiments, in block B935, the simulation device obtains a new functional. The flow then returns to block B910, where the simulation device generates a surface 972 based on the functional 971 (if the functional did not change) and on the new location or size 979B (or functional, if the functional changed).

Figure 10A:
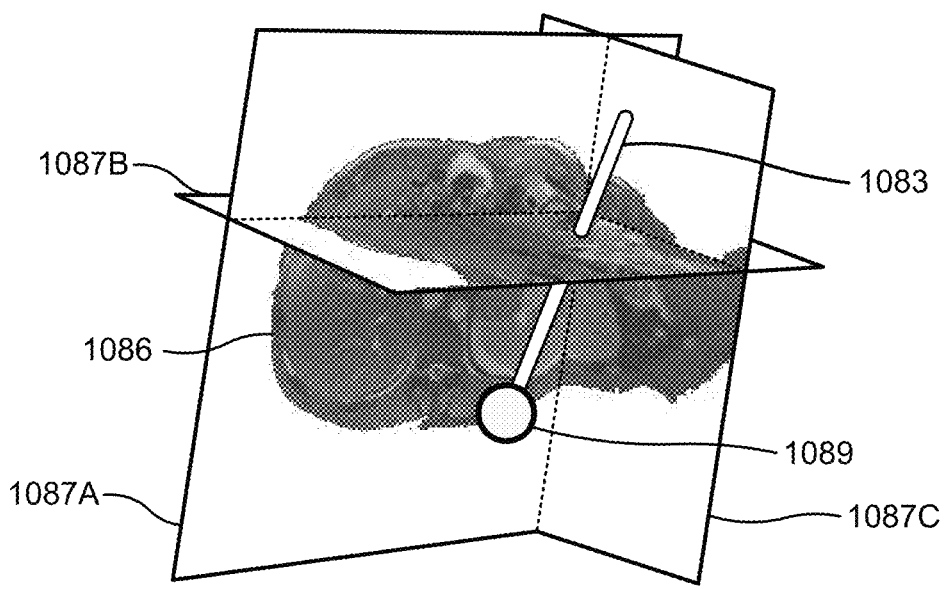
FIG. 10A illustrates an example embodiment of a visualization of an image volume.

FIG. 10A illustrates and example embodiment of a visualization. The visualization includes an ablation zone 1089, a simulated probe 1083, and a visualization of the image volume 1086. The visualization also includes three visualization planes: an axial-visualization plane 1087A, a sagittal-visualization plane 1087B, and a coronal-visualization plane 1087C. The visualization planes 1087A-C show the image data in the image volume that lies on the visualization planes 1087A-C. In FIG. 10A, the ablation zone 1089 is represented with a circle and does not include image data.

Figure 10B:
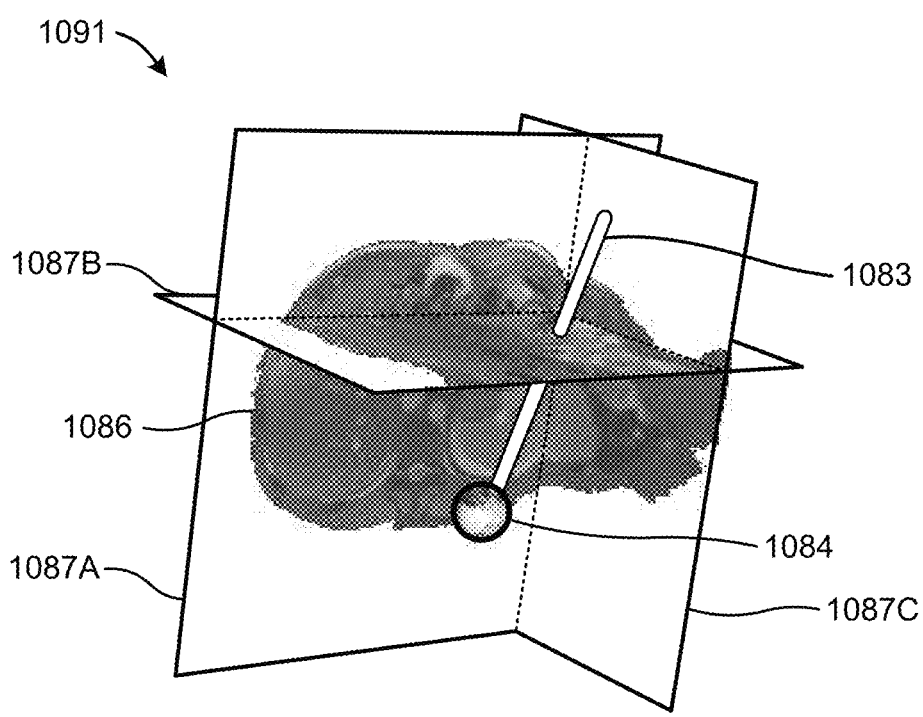
FIG. 10B illustrates an example embodiment of a combined visualization of an image volume.

FIG. 10B illustrates an example embodiment of a combined visualization 1091. The combined visualization 1091 includes a lantern 1084, a simulated probe 1083, and a visualization of an image volume 1086. The combined visualization 1091 also includes an axial-visualization plane 1087A, a sagittal-visualization plane 1087B, and a coronal-visualization plane 1087C. The lantern 1084 displays the image data that maps to the surface of an ablation zone. The lantern 1084 has an image on its surface that is generated by sampling the image volume on the ablation zone's surface (e.g., the sphere's surface), forming an image of the sampled data, and displaying the image of the sampled data on the lantern 1084.

Accordingly, the image data from the image volume is mapped to the surface of the ablation zone, and the visualization of the surface of the ablation zone simulates the appearance of the surface of a shape that has been cut out of the three-dimensional image volume. The image data may be interpolated for the points on the shape for which no image data is available (e.g., for the points on the shape that are between the image slices in the image volume).

Figure 11:
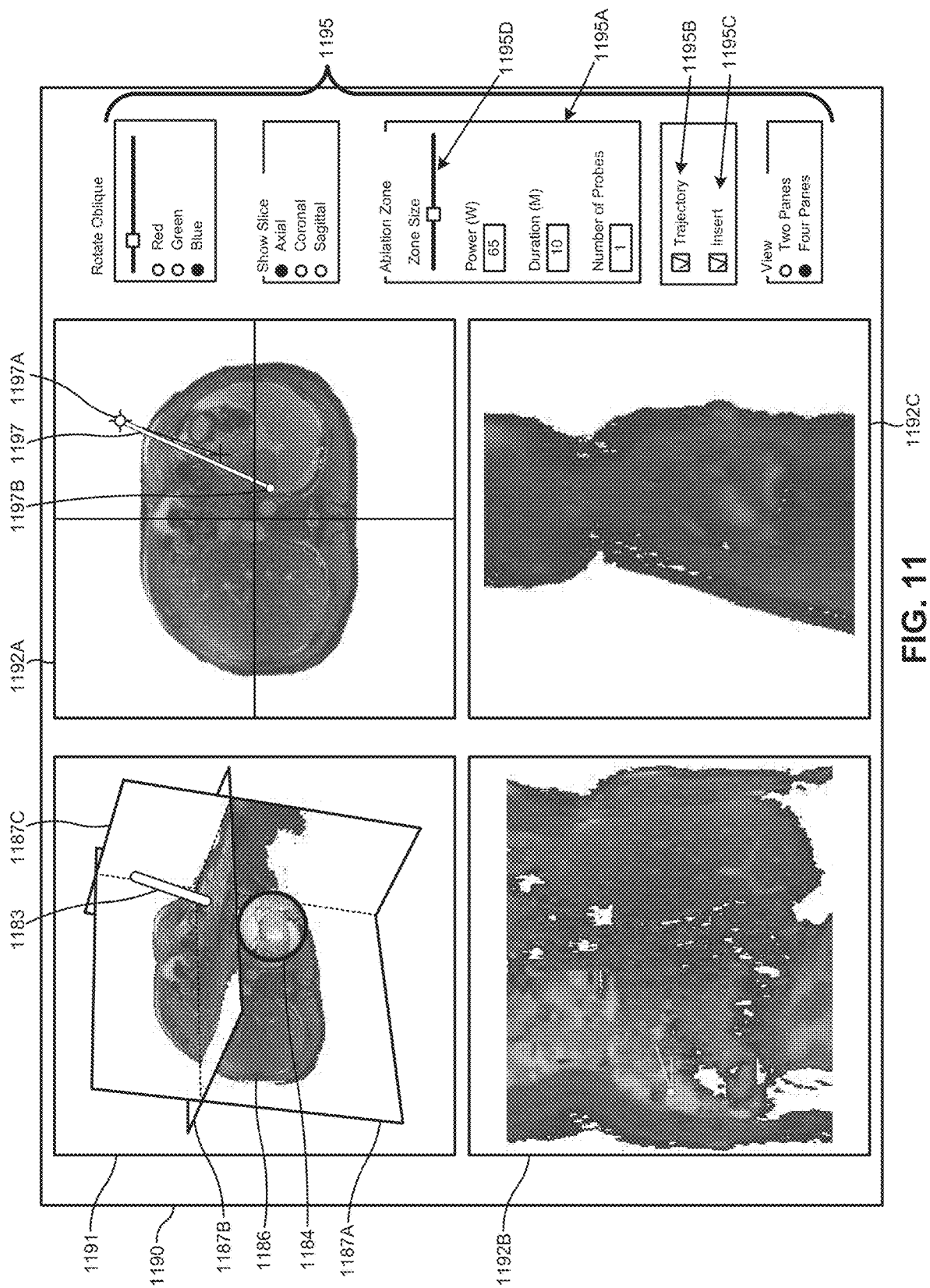
FIG. 11 illustrates an example embodiment of a user interface that includes a visualization of an ablation zone.

FIG. 11 illustrates an example embodiment of a user interface that includes a visualization of an ablation zone. The user interface 1190 includes a perspective-display area 1191 that shows a combined visualization, which includes a lantern 1184; a simulated probe 1183; image data 1186 from an image volume (e.g., an image volume on the surface (e.g., see points 1399a, 1399b, 1399c located on the surface of the lantern 1384 as shown in FIG. 13) or along a ray (e.g., the ray 385 shown in FIG. 3B; see also the ray shown in FIG. 17 with points P1 through P4; etc.) projected from the surface to another point within the shape (e.g., the ray (e.g., the ray 385 shown in FIG. 3B; see also the ray shown in FIG. 17 with points P1 through P4; etc.) may project through the lantern 1184)); an axial-visualization plane 1187A, a sagittal-visualization plane 1187B, and a coronal-visualization plane 1187C. The perspective-display area 1191 allows a user to change the viewpoint of the perspective view, for example by rotating the visualization on any axis. Additionally, the perspective-display area 1191 allows a user to change the positions of the axial-visualization plane 1187A, the sagittal-visualization plane 1187B, and the coronal-visualization plane 1187C.

The position along the normal of the visualization planes in FIG. 11 may, in one embodiment, be automatically selected by positioning a pointer over a surface position in the lantern view (see e.g., the lantern 1184). In case the lantern values are generated by sampling the image at the surface, the visualization planes may be chosen to correspond to the selected surface point. In alternative embodiments where the lantern values are generated by a function applied to a sampling of image values along a ray from the lantern surface to a predetermined location (e.g., the center of the lantern, the center of the object, etc.), the visualization planes may be selected based on the position of the representative value along the ray (for example a maximum or minimum value) according to the applied sampling function. For example, in at least one embodiment shown in FIG. 17, a visualization plane or planes may be selected depending on which one or more of the points P1 through P4 are selected as a desired viewing plane or planes.

In another embodiment the visualization planes may display, instead of a single slice, the projection of a stack of slices that span the lantern region in the corresponding view orientations (see e.g., FIGS. 2, 3A-3B, 4A-4B, 8, 11, 13, 17, etc.).

The user interface 1190 also shows an axial view 1192A, which shows the axial-visualization plane 1187A; a sagittal view 1192B, which shows the sagittal-visualization plane 1187B; and a coronal view 1192C, which shows the coronal-visualization plane 1187C. The user interface 1190 also includes controls 1195. The controls 1195 include ablation-zone controls 1195A, which allow a user to adjust a size of an ablation zone and its respective lantern 1184, a simulated power of the ablation procedure, a duration of an ablation procedure, and a number of probes and respective ablation zones. The appearance of the lantern 1184 is adjusted according to the settings of the ablation-zone controls 1195A.

The user interface 1190 also shows a trajectory 1197, which is generated in response to an activation of one of the controls 1195. In this example, the control is a trajectory checkbox 1195B. Once the trajectory checkbox 1195B is activated, the user interface 1190 allows a user to define an entry point 1197A and a target point 1197B of the trajectory 1197. The target point 1197B may be, for example, the center of a tumor. Once the entry point 1197A and the target point 1197B are defined, the user interface 1190 displays the trajectory 1197, which may indicate the insertion trajectory of a probe. Also, activating an insert control 1195C causes the user interface 1190 to display a simulated probe 1183 in place of the trajectory 1197 in the perspective-display area 1191.

The user interface 1190 also allows the lantern 1184 to be manipulated (e.g., moved, resized). This embodiment of a user interface 1190 allows a user to manipulate the lantern 1184 by moving it, rotating it, changing its size, zoom in to it, and zooming out from it. Because the lantern can be manipulated, it can be used to visualize many features that are not visible when only planes are used to view the image volume.

Also, in this embodiment the size of the lantern 1184 and its corresponding ablation zone may be changed by means of the adjustment of a zone-size control 1195D. In this embodiment, the zone-size control 1195D is a slider. The image that is presented on the lantern 1184 changes as the setting of the zone-size control 1195D changes because different image data maps to the surface of the resized ablation zone that corresponds to the lantern 1184. The generation of the lantern 1184 may be synchronized with the ablation zone's location and size. Accordingly, the lantern 1184 may be generated dynamically as the user manipulates (e.g., resizes, moves) the corresponding ablation zone of the lantern 1184.

In a related embodiment, the adjustment of the zone-size may be performed automatically, gradually changing from empty to a set maximum, which may provide a feature to view in time the contents of the lantern region. For example, in at least the embodiment shown in FIG. 17, a time lapse of several images may be shown where the first image may be an empty view of the lantern 1384 starting at a center point thereof (e.g., point P1) or another predetermined point from which the ray extends, and may expand outwardly for each additional target point (e.g., the next image may be of point P2 and data located in a radius from point P2 to P1 around the center (or other predetermined location from which the ray extends) of the lantern 1384; the following image may be of point P3 and data located in a radius from point P3 to P1 around the center (or other predetermined location from which the ray extends) of the lantern 1384; the subsequent image may then be of point P4 on the surface of the lantern 1384 and data located in a radius from point P4 to P1 around the center (or other predetermined location from which the ray extends) of the lantern 1384; etc.). In one or more embodiments, the ray 1385 may extend between at least two surface points of the lantern 1384.

Figure 12:
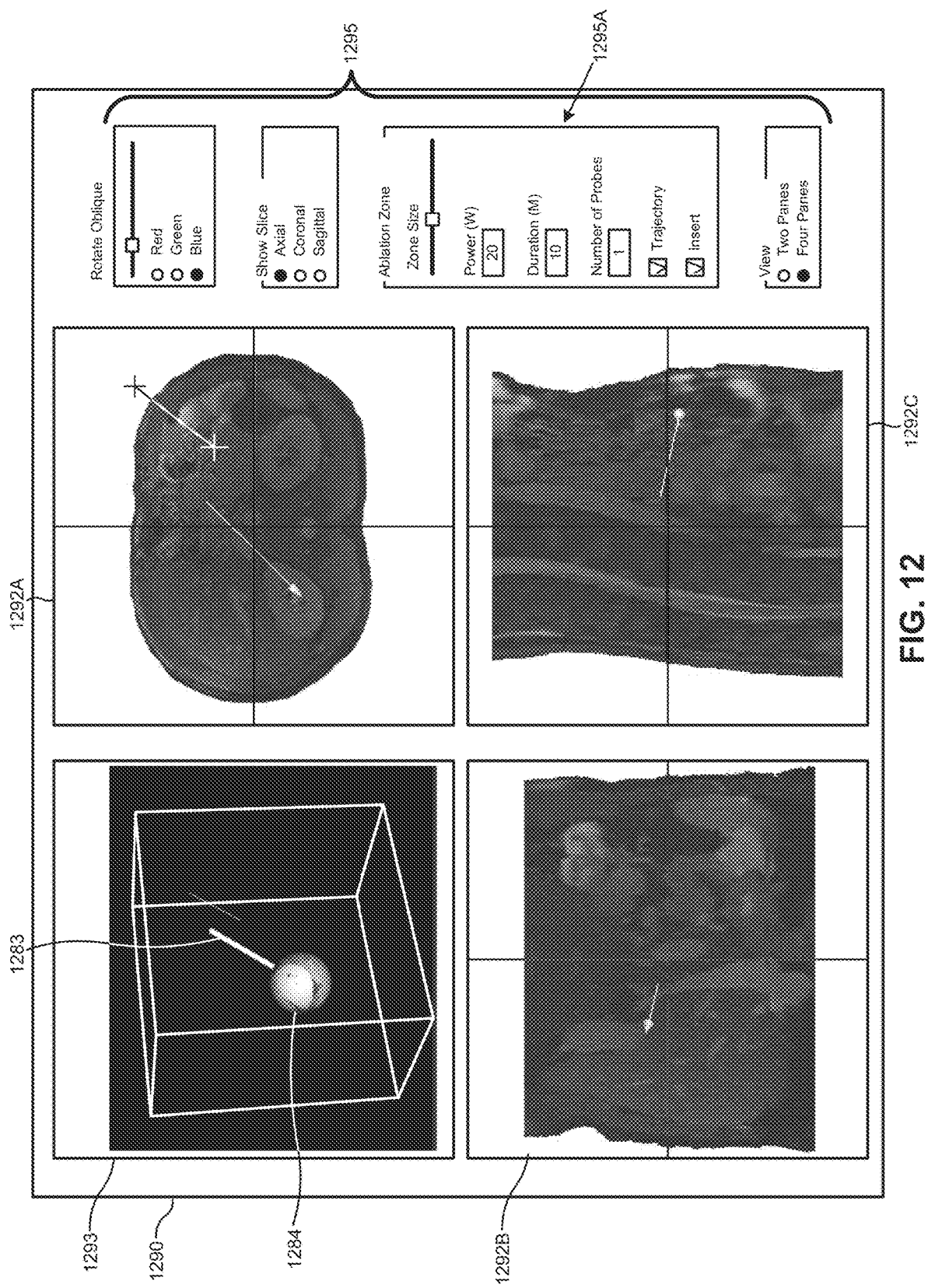
FIG. 12 illustrates an example embodiment of a user interface that includes a visualization of an ablation zone.

FIG. 12 illustrates an example embodiment of a user interface that includes a visualization of an ablation zone. The user interface 1290 includes a lantern-display area 1293, which shows a lantern 1284 and a simulated probe 1283. The user interface also includes an axial view 1292A; a sagittal view 1292B, and a coronal view 1292C. In this example embodiment, the lantern-display area 1293 shows the lantern 1284 but does not show any other image data. The user interface 1290 also includes controls 1295. The controls 1295 include ablation-zone controls 1295A, which allow a user to adjust a size of an ablation zone, a simulated power of the ablation procedure, a duration of an ablation procedure, and a number of probes and respective ablation zones.

FIG. 13 illustrates an example embodiment of a user interface that includes a visualization of an ablation zone. The user interface 1390 includes a perspective-display area 1391, which shows a lantern 1384; a simulated probe 1383; and image data 1386. The perspective-display area 1391 also includes an axial-visualization plane 1387A, a sagittal-visualization plane 1387B, and a coronal-visualization plane 1387C. The user interface also shows an axial view 1392, which shows the axial-visualization plane 1387A. Additionally, as shown in FIG. 13, the user interface 1390 includes controls 1395.

Figure 14A:
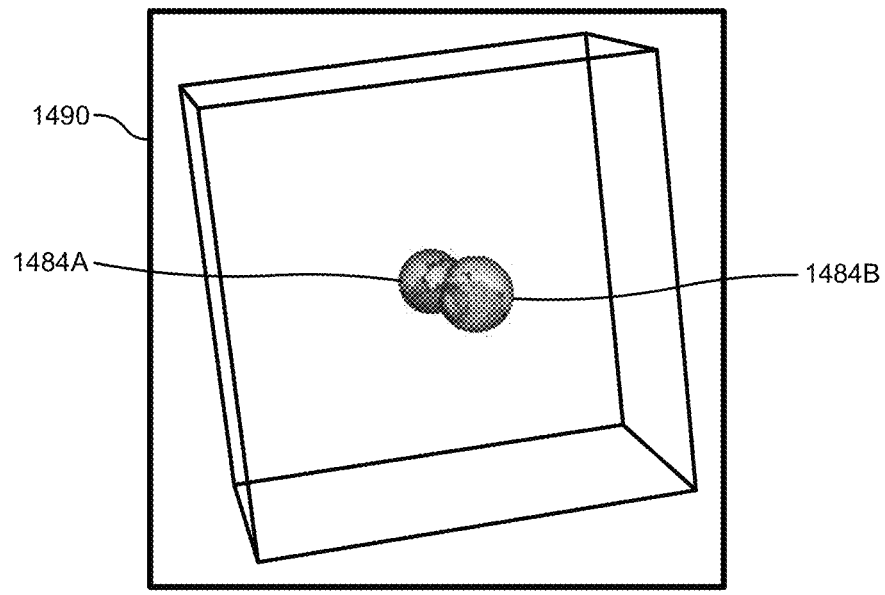
FIG. 14A illustrates an example embodiment of a user interface that includes a visualization of an ablation zone.

FIG. 14A illustrates an example embodiment of a user interface that includes a visualization of an ablation zone. The user interface 1490 presents a visualization that includes a first lantern 1484A and a second lantern 1484B.

Figure 14B:
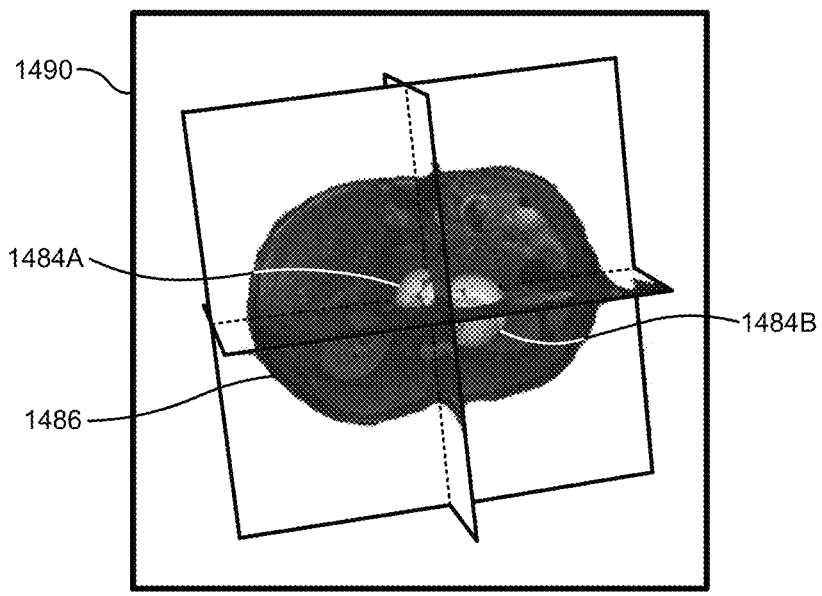
FIG. 14B illustrates an example embodiment of a user interface that includes a visualization of an ablation zone.

FIG. 14B illustrates an example embodiment of a user interface that includes a visualization of an ablation zone. The user interface 1490 presents a combined visualization that includes a first lantern 1484A, a second lantern 1484B, and image data 1486.

Figure 15A:
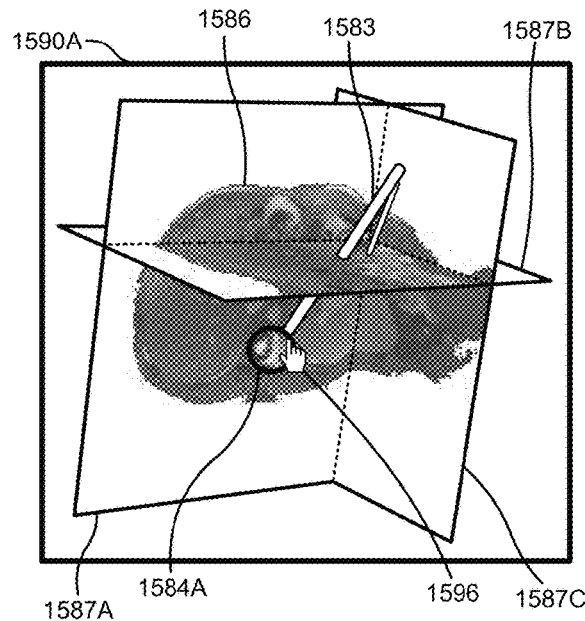
FIG. 15A illustrates an example embodiment of a user interface that includes a visualization of an ablation zone.

FIG. 15A illustrates an example embodiment of a user interface that includes a visualization of an ablation zone. The user interface 1590A shows a lantern 1584A, image data 1586, a simulated probe 1583, a cursor 1596, an axial-visualization plane 1587A, a sagittal-visualization plane 1587B, and a coronal-visualization plane 1587C. A user can use the cursor 1596 to reposition the lantern 1584A and its corresponding ablation zone.

Figure 15B:
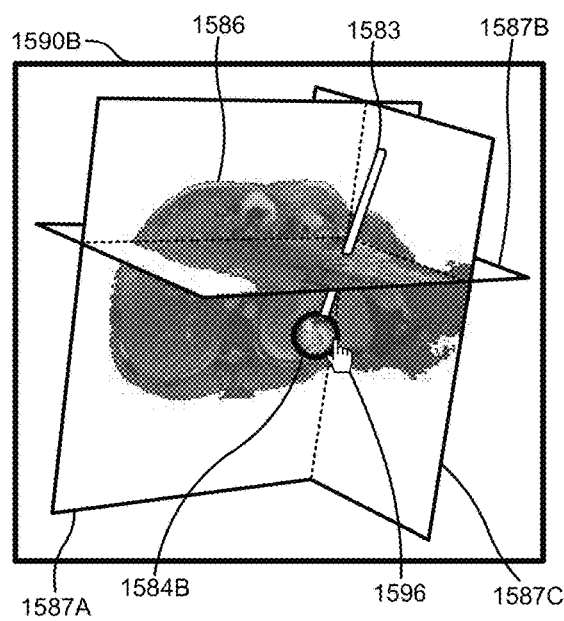
FIG. 15B illustrates an example embodiment of a user interface that includes a visualization of an ablation zone.

FIG. 15B illustrates an example embodiment of a user interface that presents a visualization of an ablation zone. The user interface 1590B shows a lantern 1584B, image data 1586, a simulated probe 1583, a cursor 1596, an axial-visualization plane 1587A, a sagittal-visualization plane 1587B, and a coronal-visualization plane 1587C. Because the cursor 1596 was used to reposition the lantern 1584A in FIG. 15A to the position in FIG. 15B, the lantern 1584B in FIG. 15B has a different location than the lantern 1584A in FIG. 15A. Consequently, these lanterns have different appearances because the image data that was sampled when the lantern 1584A in FIG. 15A was generated is different from at least some of the image data that was sampled when the lantern 1584B in FIG. 15B was generated, even though both lanterns were generated from the same image volume.

Figure 15C:
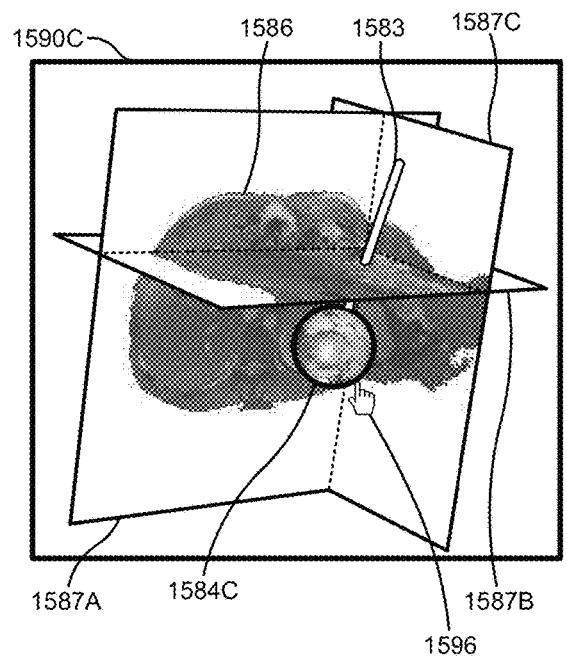
FIG. 15C illustrates an example embodiment of a user interface that includes a visualization of an ablation zone.

FIG. 15C illustrates an example embodiment of a user interface that includes a visualization of an ablation zone. The user interface 1590C shows a lantern 1584C, image data 1586, a simulated probe 1583, a cursor 1596, an axial-visualization plane 1587A, a sagittal-visualization plane 1587B, and a coronal-visualization plane 1587C. This lantern 1584C has a different size than the lantern 1584B in FIG. 15B, and consequently has a different appearance because at least some of the image data that was sampled when the lantern 1584B in FIG. 15B was generated is different from the image data that was sampled when the lantern 1584C in FIG. 15C was generated.

Figure 15D:
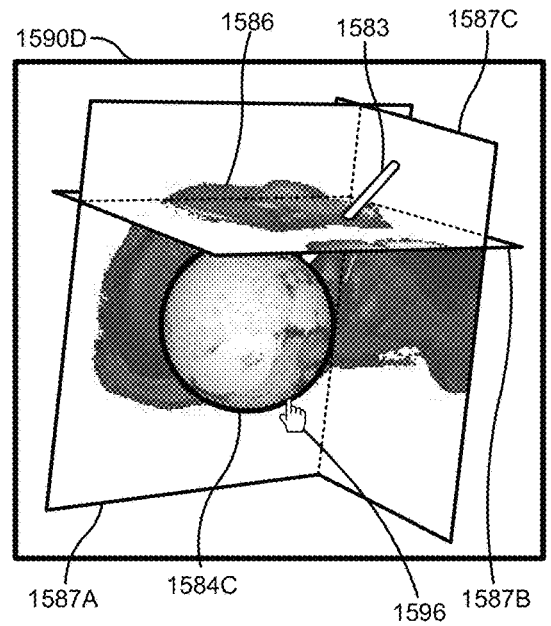
FIG. 15D illustrates an example embodiment of a user interface that includes a visualization of an ablation zone.

FIG. 15D illustrates an example embodiment of a user interface that includes a visualization of an ablation zone. The user interface 1590D shows a lantern 1584D, image data 1586, a cursor 1596, an axial-visualization plane 1587A, a sagittal-visualization plane 1587B, and a coronal-visualization plane 1587C. This lantern 1584D has a different size and a different location than the lantern 1584C in FIG. 15C, and consequently has a different appearance because at least some of the image data that was sampled when the lantern 1584C in FIG. 15C was generated is different from the image data that was sampled when the lantern 1584D in FIG. 15D was generated.

In this embodiment, the respective locations of the axial-visualization plane 1587A, the sagittal-visualization plane 1587B, and the coronal-visualization plane 1587C are different than the respective locations of the axial-visualization plane 1587A, the sagittal-visualization plane 1587B, and the coronal-visualization plane 1587C in FIG. 15C. Consequently, the appearances of the axial-visualization plane 1587A, the sagittal-visualization plane 1587B, and the coronal-visualization plane 1587C are not the same in FIGS. 15C-D because they show different image data in FIGS. 15C-D.

Figure 16:
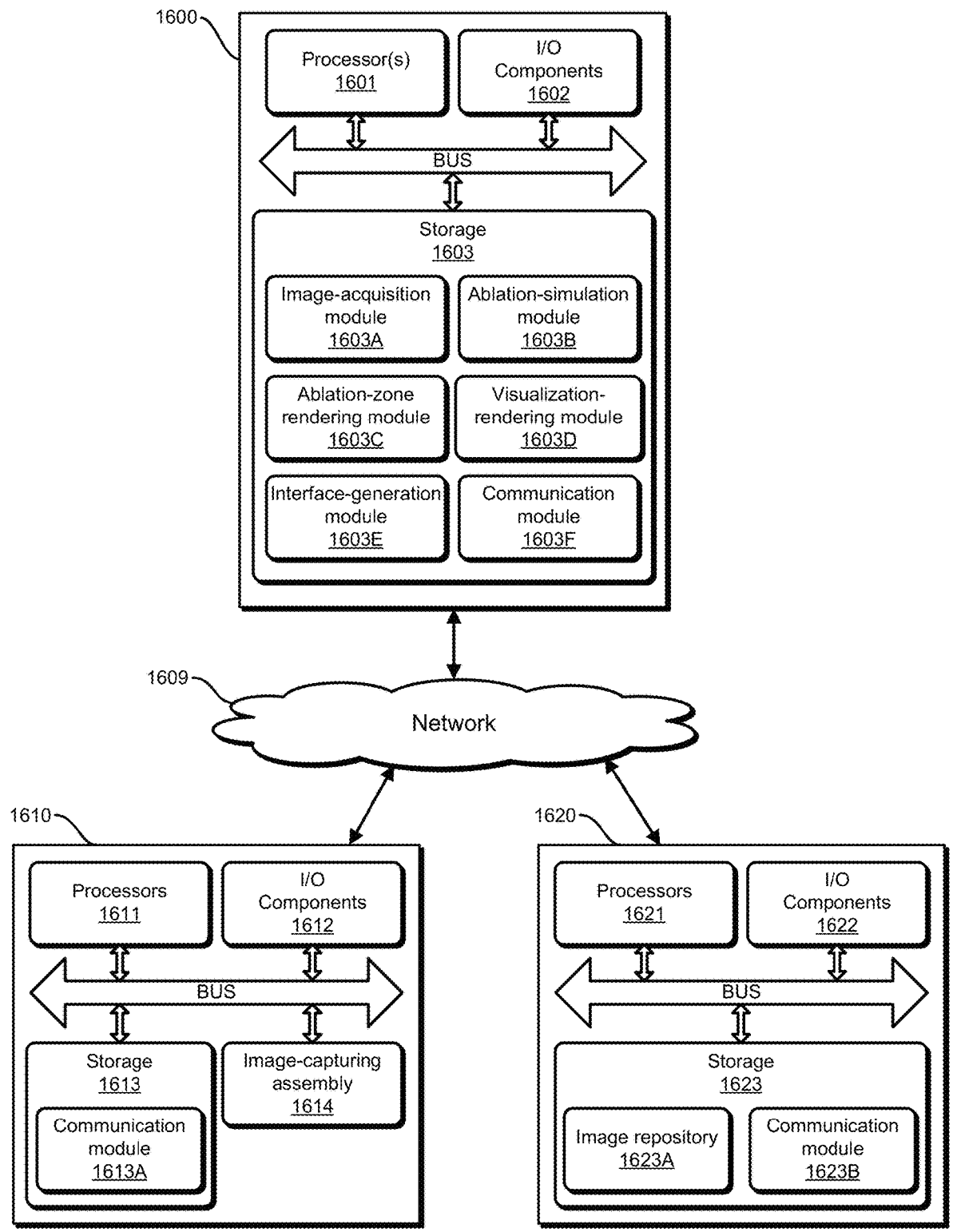
FIG. 16 illustrates an example embodiment of a system for simulating and visualizing an ablation zone.

FIG. 16 illustrates an example embodiment of a system for simulating and visualizing an ablation zone. The system includes a simulation device 1600, which is a specially-configured computing device; an image-capturing device 1610; and an image server 1620. In this embodiment, the devices communicate by means of one or more networks 1609, which may include a wired network, a wireless network, a LAN, a WAN, a MAN, and a PAN. Also, in some embodiments the devices communicate by means of other wired or wireless channels.

The simulation device 1600 includes one or more processors 1601, one or more I/O components 1602, and storage 1603. Also, the hardware components of the simulation device 1600 communicate by means of one or more buses or other electrical connections. Examples of buses include a universal serial bus (USB), an IEEE 1394 bus, a PCI bus, an Accelerated Graphics Port (AGP) bus, a Serial AT Attachment (SATA) bus, and a Small Computer System Interface (SCSI) bus.

The one or more processors 1601 include one or more central processing units (CPUs), which include microprocessors (e.g., a single core microprocessor, a multi-core microprocessor); one or more graphics processing units (GPUs); one or more application-specific integrated circuits (ASICs); one or more field-programmable-gate arrays (FPGAs); one or more digital signal processors (DSPs); or other electronic circuitry (e.g., other integrated circuits). The I/O components 1602 include communication components (e.g., a GPU, a network-interface controller) that communicate with input and output devices, which may include a keyboard, a display device, a mouse, a printing device, a touch screen, a light pen, an optical-storage device, a scanner, a microphone, a drive, a controller (e.g., a joystick, a control pad), and the network 1609. In some embodiments, the I/O components 1602 also include specially-configured communication components that communicate with the image-capturing device 1610.

The storage 1603 includes one or more computer-readable storage media. As used herein, a computer-readable storage medium, in contrast to a mere transitory, propagating signal per se, refers to a computer-readable media that includes an article of manufacture, for example a magnetic disk (e.g., a floppy disk, a hard disk), an optical disc (e.g., a CD, a DVD, a Blu-ray), a magneto-optical disk, magnetic tape, and semiconductor memory (e.g., a non-volatile memory card, flash memory, a solid-state drive, SRAM, DRAM, EPROM, EEPROM). Also, as used herein, a transitory computer-readable medium refers to a mere transitory, propagating signal per se, and a non-transitory computer-readable medium refers to any computer-readable medium that is not merely a transitory, propagating signal per se. The storage 1603, which may include both ROM and RAM, can store computer-readable data or computer-executable instructions.

The simulation device 1600 also includes an image-acquisition module 1603A, an ablation-simulation module 1603B, an ablation-zone-rendering module 1603C, a visualization-rendering module 1603D, an interface-generation module 1603E, and a communication module 1603F. A module includes logic, computer-readable data, or computer-executable instructions, and may be implemented in software (e.g., Assembly, C, C++, C#, Java, BASIC, Perl, Visual Basic), hardware (e.g., customized circuitry), or a combination of software and hardware. In some embodiments, the devices in the system include additional or fewer modules, the modules are combined into fewer modules, or the modules are divided into more modules. When the modules are implemented in software, the software can be stored in the storage 1603.

The image-acquisition module 1603A includes instructions that, when executed, or circuits that, when activated, cause the simulation device 1600 to obtain one or more image volumes from the image-capturing device 1610 or the image server 1620, for example as described in block B610 in FIG. 6, in block B715 in FIG. 7, or in block B915 in FIG. 9.

The ablation-simulation module 1603B includes instructions that, when executed, or circuits that, when activated, cause the simulation device 1600 to calculate a size and shape of an ablation zone based on one or more of a time of an ablation procedure, a power of the ablation procedure, a shape of the ablation zone, and the composition of the material that will be ablated. In some embodiments, the size and shape of the ablation zone is modeled by a functional. Also, in some embodiments, these operations include the operations in blocks B600 and B605 in FIG. 6; in blocks B700, B705, and B710 in FIG. 7; or in blocks B900, B905, and B910 in FIG. 9.

The ablation-zone rendering module 1603C includes instructions that, when executed, or circuits that, when activated, cause the simulation device 1600 to sample image data in an image volume that lies on the surface of an ablation zone and by generating a lantern, which includes an image of the sampled image data. In some embodiments, these operations include the operations that are described in blocks B615, B620, and B625 in FIG. 6; in blocks B720, B725, and B730 in FIG. 7; or in blocks B920 and B925 in FIG. 9.

The visualization-rendering module 1603D includes instructions that, when executed, or circuits that, when activated, cause the simulation device 1600 to generate a visualization of an image volume and a lantern, for example as described in blocks B630 and B635 in FIG. 6 or in blocks B735 and B740 in FIG. 7.

The interface-generation module 1603E includes instructions that, when executed, or circuits that, when activated, cause the simulation device 1600 to generate a menu and receive commands from the menu.

The communication module 1603F includes instructions that, when executed, or circuits that, when activated, cause the simulation device 1600 to communicate with one or more other devices, for example the image-capturing device 1610 and the image server 1620.

The image-capturing device 1610 includes one or more processors 1611, one or more I/O components 1612, storage 1613, a communication module 1613A, and an image-capturing assembly 1614. The image-capturing assembly 1614 includes one or more image sensors, one or more lenses, and an aperture. The communication module 1613A includes instructions that, when executed, or circuits that, when activated, cause the image-capturing device 1610 to capture an image, receive a request for an image from a requesting device, retrieve a requested image from the storage 1613, or send a retrieved image to the requesting device (e.g., the simulation device 1600).

The image server 1620 includes one or more processors 1621, one or more I/O components 1622, and storage 1623. The storage includes an image repository 1623A, which stores images, and a communication module 1623B. The communication module 1623B includes instructions that, when executed, or circuits that, when activated, cause the image server 1620 to receive a request for an image from a requesting device, retrieve a requested image from the image repository 1623A, or send a retrieved image to the requesting device (e.g., the simulation device 1600).

At least some of the above-described devices, systems, and methods can be implemented, at least in part, by providing one or more computer-readable media that contain computer-executable instructions for realizing the above-described operations to one or more computing devices that are configured to read and execute the computer-executable instructions. The systems or devices perform the operations of the above-described embodiments when executing the computer-executable instructions. Also, an operating system on the one or more systems or devices may implement at least some of the operations of the above-described embodiments.

Furthermore, some embodiments use one or more functional units to implement the above-described devices, systems, and methods. The functional units may be implemented in only hardware (e.g., customized circuitry) or in a combination of software and hardware (e.g., a microprocessor that executes software).

The scope of the claims is not limited to the above-described embodiments and includes various modifications and equivalent arrangements. Also, as used herein, the conjunction "or" generally refers to an inclusive "or," though "or" may refer to an exclusive "or" if expressly indicated or if the context indicates that the "or" must be an exclusive "or.

The invention claimed is:

1. A device comprising:
one or more processors that operate to:
obtain an image volume;
obtain a description of a surface that includes a shape of the surface, a size of the surface, and a location of the surface in the image volume;
sample the image volume in a first mode or a second mode of two modes such that sampled surface-image data is or are produced;
generate a visualization of the sampled surface-image data that defines one or more lanterns, each of the one or more lanterns being a visualization of a surface of a respective target zone of or in the image volume, the respective target zone being a volume that is to be affected by a medical procedure; and
displaying the one or more lanterns on a display of the device such that: (i) the one or more lanterns are overlaid on the image volume; and (ii) the one or more lanterns each include a respective image on its surface where the respective image maps to and displays a surface of the respective target zone,
wherein:
(i) in the event that the one or more processors operate in the first mode for sampling the image volume, the one or more processors sample the image volume on the surface; or
(ii) in the event that the one or more processors operate in the second mode for sampling the image volume, the one or more processors sample the image volume along a ray projected from the surface to another predetermined point within the shape.

2. The device of claim 1, wherein the one or more processors further operate to
generate a visualization of a part of the image volume that is not included in the visualization of the sampled surface-image data.

3. The device of claim 2, wherein the one or more processors further operate to
generate an interface that includes the visualization of the sampled surface-image data and includes the visualization of the part of the image volume that is not included in the visualization of the sampled surface-image data.

4. The device of claim 1, wherein one or more of the following:
(i) the description of the surface includes one or more functionals;
(ii) the one or more functionals model the respective target zones such that the one or more lanterns are generated from the one or more functionals;
(iii) the one or more functionals model the respective target zones as ablation zones;
(iv) the sampled surface having the description is a surface of the one or more functionals; and/or (v) in a case where the one or more functionals comprises a first functional and a second functional and the first functional and the second functional overlap, the first functional and the second functional are merged into a single surface and/or are merged to define the sampled surface.

5. The device of claim 1, wherein the one or more processors further operate to obtain a modified surface that has a different position in the image volume, a different shape, or a different size;

sample the image volume on the modified surface, or along a ray projected from the modified surface to another predetermined point within the shape, such that modified sampled surface-image data is or are produced, wherein at least some of the modified sampled surface-image data is different from the sampled surface-image data; and generate a visualization of the modified sampled surface-image data.

6. The device of claim 1, wherein the one or more processors further operate to one or more of the following:

(i) use the obtained image volume, the sampled surface-image data, and/or the generated visualization to generate segmentation maps that label whether each voxel of the image volume, the sampled surface-image data, and/or the generated visualization is part or not of one or more defined anatomical structures; and/or (ii) overlay the segmentation maps on the generated visualization, or use the segmentation maps for masking the image volume, the sampled surface-image data and/or the generated visualization.

7. The device of claim 1, wherein the one or more processors further operate to one or more of the following:

(i) calculate one or more lantern values from a function applied to the sampling of data points along a ray from a surface of a lantern of the one or more lanterns to another point in a region of the lantern;

(ii) calculate one or more lantern values from the function applied to the sampling of data points along the ray from a surface of the lantern of the one or more lanterns to another point in a region of the lantern, wherein the region of the lantern is one or more of: a center of the lantern, another surface point of the lantern, and a point selected by a user of the device in the visualization of the lantern;

(iii) use, as the function, one of the following: a maximum value of the sampling of data points, an average value of the sampling of data points, and a minimum value of the sampling of data points; and/or (iv) display a value with the one or more lanterns, where the value is relative to a sampling of segmentation maps on the surface of the lantern or along a ray from the surface to another point in the lantern region such that the value indicates whether a segmented anatomical region is contained in the sampled points or contained in the distance from the surface of the anatomical region to the surface of the lantern.

8. The device of claim 7, wherein the one or more processors further operate to one or more of the following:

(i) automatically select a surface point of the lantern of the one or more lanterns from the visualization or from a user of the device;

(ii) in a case where the one or more lantern values are generated by sampling the image volume at the surface, choose visualization planes corresponding to the selected surface point of the lantern, or, in a case where the one or more lantern values are generated by the function applied to the sampling of image values along the ray from the lantern surface to the another point in the region of the lantern, choose visualization planes based on the position of a representative value along the ray, where the representative value is based on the applied function;

(iii) choose the visualization planes as a projection of a stack of slices that span the region of the lantern in corresponding view orientations, or as a single slice; and/or (iv) adjust the image volume or the region of the lantern automatically, gradually changing from empty to a set maximum, such that the user of the device can view in time the content or contents of the region of the lantern.

9. The device of claim 1, wherein the one or more processors further operate to move, reshape, and/or resize the one or more lanterns with a cursor on the display.

10. The device of claim 1, wherein one or more of the following:

(i) the respective image on the one or more lanterns simulates or displays an appearance of a respective portion that has been cut out of or removed from the image volume;

(ii) the respective image on the one or more lanterns displays the respective portion of the image volume that is located underneath the overlaid one or more lanterns;

(iii) the respective image on the one or more lanterns displays one or more features that intersect with the respective target zone;

(iv) the respective image of the one or more lanterns operates to be used for planning and/or performing the medical procedure; and/or (v) the medical procedure is ablation.

11. The device of claim 1, wherein the one or more lanterns are generated based on one or more color maps in addition to the sampled surface-image data.

12. A method comprising:

obtaining an image volume, wherein the image volume is composed of an image stack;

sampling the image volume in a first mode or a second mode of two modes such that first sampled surface-image data is or are produced;

generating a visualization of the first sampled surface-image data that defines one or more lanterns, each of the one or more lanterns being a visualization of a surface of a respective target zone of or in the image volume, the respective target zone being a volume that is to be affected by a medical procedure; and displaying the one or more lanterns on a display such that: (i) the one or more lanterns are overlaid on the image volume; and (ii) the one or more lanterns each include a respective image on its surface where the respective image maps to and displays a surface of the respective target zone, wherein:

(i) in the event that the sampling step uses the first mode for sampling the image volume, the sampling step samples the image volume on the surface; or (ii) in the event that the sampling step uses the second mode for sampling the image volume, the sampling step samples the image volume along a ray projected from the surface to another predetermined point within the shape.

13. The method of claim 12, further comprising:

sampling the image volume on a second surface that has a different size than the first surface, a different shape than the first surface, or a different position than the first surface, or along a ray projected from the second surface to another predetermined point within the image volume or within the different size of the second surface, such that second sampled surface-image data is or are produced;

generating a visualization of the second sampled surface-image data that defines one or more other lanterns, each of the one or more other lanterns being a visualization of a surface of a respective other target zone of or in the image volume, the respective other target zone being a volume that is to be affected by a medical procedure; and displaying the one or more other lanterns on the display such that: (i) the one or more other lanterns are overlaid on the image volume; and (ii) the one or more lanterns each include a respective image on its surface where the respective image maps to and displays a surface of the respective other target zone.

14. The method of claim 13, further comprising:
generating an interface that includes the visualization of the first sampled surface-image data and includes the visualization of the second sampled surface-image data on the display.

15. The method of claim 14, wherein one or more of the following: (i) the interface further includes an axial-image plane, a sagittal-image plane, and a coronal-image plane on the display; (ii) the interface further includes an image on the display, the image having the axial-image plane, the sagittal-image plane, and the coronal-image plane intersect with each other through or in the image volume; (iii) the interface further includes a lantern display area which shows one or more of the following: a simulated probe, the one or more lanterns, and/or the one or more other lanterns; and/or (iv) the respective target zone is an ablation zone.

16. The method of claim 15, wherein one or more of the following:
(i) the interface operates to display a trajectory of the simulated probe;
(ii) the interface operates to allow input to define an entry point and a target point of the trajectory;
(iii) the entry point and the target point operate to define the trajectory of the simulated probe;
(iv) the interface operates to display the simulated probe in place of the trajectory; and/or
(v) the interface operates to display the trajectory and/or the simulated probe in the axial-image plane and/or in the image having the axial-image plane, the sagittal-image plane, and the coronal-image plane intersect with each other through or in the image volume.

17. The method of claim 12, wherein the sampling of the image volume on the first surface includes one or more of the following: (i) interpolating image data based on the image volume and based on the first surface, wherein the interpolated image data is included in the first sampled surface-image data; and/or (ii) interpolating the image data to include data points that are disposed on or along the first surface in any area where the first surface is not close to data points in the image volume.

18. The method of claim 12, further comprising one or more of the following:
(i) using the obtained image volume, the sampled first surface-image data, and/or the generated visualization to generate segmentation maps that label whether each voxel of the image volume, the sampled first surface-image data, and/or the generated visualization is part or not of one or more defined anatomical structures; and/or
(ii) overlaying the segmentation maps on the generated visualization, or use the segmentation maps for masking the image volume, the sampled first surface-image data and/or the generated visualization.

19. The method of claim 12, further comprising one or more of the following:
(i) calculating one or more lantern values from a function applied to the sampling of data points along a ray from a surface of a lantern of the one or more lanterns to another point in a region of the lantern;
(ii) calculating one or more lantern values from the function applied to the sampling of data points along the ray from a surface of the lantern of the one or more lanterns to another point in a region of the lantern, wherein the region of the lantern is one or more of: a center of the lantern, another surface point of the lantern, and a point selected by a user of the device in the visualization of the lantern;
(iii) using, as the function, one of the following: a maximum value of the sampling of data points, an average value of the sampling of data points, and a minimum value of the sampling of data points; and/or
(iv) displaying a value with the one or more lanterns, where the value is relative to a sampling of segmentation maps on the surface of the lantern or along a ray from the surface to another point in the lantern region such that the value indicates whether a segmented anatomical region is contained in the sampled points or contained in the distance from the surface of the anatomical region to the surface of the lantern.

20. The method of claim 19, further comprising one or more of the following:
(i) automatically selecting a surface point of the lantern of the one or more lanterns from the visualization or from a user of the device;
(ii) in a case where the one or more lantern values are generated by sampling the image volume at the surface, choosing visualization planes corresponding to the selected surface point of the lantern, or, in a case where the one or more lantern values are generated by the function applied to the sampling of image values along the ray from the lantern surface to the another point in the region of the lantern, choosing visualization planes based on the position of a representative value along the ray, where the representative value is based on the applied function;
(iii) choosing the visualization planes as a projection of a stack of slices that span the region of the lantern in corresponding view orientations, or as a single slice; and/or
(iv) adjusting the image volume or the region of the lantern automatically, gradually changing from empty to a set maximum, such that the user of the device can view in time the content or contents of the region of the lantern.

21. One or more computer-readable storage media storing instructions that, when executed by one or more processors, cause the one or more processors to perform a method, the method comprising:
obtaining an image volume, wherein the image volume is composed of an image stack;
sampling the image volume in a first mode or a second mode of two modes such that first sampled surface-image data is or are produced;

generating an image of the first sampled surface-image data that defines one or more lanterns, each of the one or more lanterns being a visualization of a surface of a respective target zone of or in the image volume, the respective target zone being a volume that is to be affected by a medical procedure; and displaying the one or more lanterns on a display such that: (i) the one or more lanterns are overlaid on the image volume; and (ii) the one or more lanterns each include a respective image on its surface where the respective image maps to and displays a surface of the respective target zone, wherein:

(i) in the event that the sampling step uses the first mode for sampling the image volume, the sampling step samples the image volume on the surface; or (ii) in the event that the sampling step uses the second mode for sampling the image volume, the sampling step samples the image volume along a ray projected from the surface to another predetermined point within the shape.

22. The one or more computer-readable storage media of claim 21, wherein the method further comprises:

obtaining a new setting for the medical procedure that corresponds to the respective target zone;

modifying the first surface based on the new setting, such that a modified first surface is generated;

sampling the image volume on the modified first surface, or along a ray projected from the modified first surface to another predetermined point within the image volume or within a shape of the first surface, such that modified first sampled surface-image data is or are produced, where at least some of the modified first sampled surface-image data is different from the first sampled surface-image data; and generating an image of the modified first sampled surface-image data.

23. The one or more computer-readable storage media of claim 21, wherein the method further comprises:

obtaining information that describes a second surface, wherein the second surface models a corresponding respective target zone;

sampling the image volume on the second surface, or along a ray projected from the second surface to another predetermined point within the image volume or within a shape of the second surface, such that second sampled surface-image data is or are produced; and generating an image of the second sampled surface-image data.

24. The one or more computer-readable storage media of claim 21, wherein the surface has a shape of a sphere or an ellipsoid.

25. The one or more computer-readable storage media of claim 21, wherein the method further comprises:

generating an interface that includes the image of the first sampled surface-image data on the display.

26. The one or more computer-readable storage media of claim 25, wherein one or more of the following: (i) the interface also displays an image of at least part of the image volume that is not included in the image of the first sampled surface-image data; (ii) the interface further includes an axial-image plane, a sagittal-image plane, and a coronal-image plane on the display; (iii) the interface further includes an image on the display, the image having the axial-image plane, the sagittal-image plane, and the coronal-image plane intersect with each other through or in the image volume; (iv) the interface further includes a lantern display area which shows one or more of the following: a simulated probe, the one or more lanterns, and/or the one or more other lanterns; and/or (v) the respective target zone is an ablation zone.

27. The one or more computer-readable storage media of claim 21, wherein the method further comprises one or more of the following:

(i) using the obtained image volume, the sampled first surface-image data, and/or the generated image to generate segmentation maps that label whether each voxel of the image volume, the sampled first surface-image data, and/or the generated image is part or not of one or more defined anatomical structures; and/or (ii) overlaying the segmentation maps on the generated image, or use the segmentation maps for masking the image volume, the sampled first surface-image data and/or the generated image.

28. The one or more computer-readable storage media of claim 21, wherein the method further comprises one or more of the following:

(i) calculating one or more lantern values from a function applied to the sampling of data points along a ray from a surface of a lantern of the one or more lanterns to another point in a region of the lantern;

(ii) calculating one or more lantern values from the function applied to the sampling of data points along the ray from a surface of the lantern of the one or more lanterns to another point in a region of the lantern, wherein the region of the lantern is one or more of: a center of the lantern, another surface point of the lantern, and a point selected by a user of the device in the visualization of the lantern;

(iii) using, as the function, one of the following: a maximum value of the sampling of data points, an average value of the sampling of data points, and a minimum value of the sampling of data points; and/or (iv) displaying a value with the one or more lanterns, where the value is relative to a sampling of segmentation maps on the surface of the lantern or along a ray from the surface to another point in the lantern region such that the value indicates whether a segmented anatomical region is contained in the sampled points or contained in the distance from the surface of the anatomical region to the surface of the lantern.

29. The one or more computer-readable storage media of claim 28, wherein the method further comprises one or more of the following:

(i) automatically selecting a surface point of the lantern of the one or more lanterns from the image or from a user of the device;

(ii) in a case where the one or more lantern values are generated by sampling the image volume at the surface, choosing visualization planes corresponding to the selected surface point of the lantern, or, in a case where the one or more lantern values are generated by the function applied to the sampling of image values along the ray from the lantern surface to the another point in the region of the lantern, choosing visualization planes based on the position of a representative value along the ray, where the representative value is based on the applied function;

(iii) choosing the visualization planes as a projection of a stack of slices that span the region of the lantern in corresponding view orientations, or as a single slice; and/or (iv) adjusting the image volume or the region of the lantern automatically, gradually changing from empty to a set maximum, such that the user of the device can view in time the content or contents of the region of the lantern.

\* \* \* \* \*